United States Patent
Albert et al.

(10) Patent No.: US 8,546,112 B2
(45) Date of Patent: Oct. 1, 2013

(54) PROCESS FOR THE STEREOSELECTIVE ENZYMATIC HYDROLYSIS OF 5-METHYL-3-NITROMETHYL-HEXANOIC ACID ESTER

(75) Inventors: Martin Albert, Kundl (AT); Ferdinand Zepeck, Kundl (AT); Andreas Berger, Kundl (AT); Waander Riethorst, Kundl (AT); Helmut Schwab, Graz (AT); Daniel Luschnig, Graz (AT); Peter Remler, Graz (AT); Joerg Salchenegger, Kundl (AT); Doris Osl, Kundl (AT); Dominic De Souza, Kundl (AT)

(73) Assignee: Sandoz AG, Basel (CH)

( * ) Notice: Subject to any disclaimer, the term of this patent is extended or adjusted under 35 U.S.C. 154(b) by 191 days.

(21) Appl. No.: 12/993,132

(22) PCT Filed: May 19, 2009

(86) PCT No.: PCT/EP2009/056099
§ 371 (c)(1),
(2), (4) Date: Mar. 2, 2011

(87) PCT Pub. No.: WO2009/141362
PCT Pub. Date: Nov. 26, 2009

(65) Prior Publication Data
US 2011/0165636 A1    Jul. 7, 2011

Related U.S. Application Data

(60) Provisional application No. 61/128,371, filed on May 21, 2008.

(51) Int. Cl.
C12P 13/04    (2006.01)

(52) U.S. Cl.
USPC ........... 435/106; 435/136; 435/196; 435/197; 435/198

(58) Field of Classification Search
USPC .......................... 435/136, 196, 197, 198, 106
See application file for complete search history.

(56) References Cited

U.S. PATENT DOCUMENTS

| | | | | |
|---|---|---|---|---|
| 4,745,200 A | * | 5/1988 | Moeller | ........................ 549/450 |
| 5,637,767 A | | 6/1997 | Grote | |
| 2003/0170837 A1 | * | 9/2003 | Bramucci et al. | ............. 435/146 |
| 2007/0141684 A1 | | 6/2007 | Evans | |

FOREIGN PATENT DOCUMENTS

| | | |
|---|---|---|
| EP | 828704 A | 12/1996 |
| EP | 830338 A | 12/1996 |
| WO | 9638405 A1 | 12/1996 |
| WO | 9640617 A1 | 12/1996 |
| WO | 0155090 A1 | 8/2001 |
| WO | 2003062185 A1 | 7/2003 |
| WO | 2005087370 A1 | 9/2005 |
| WO | 2005100580 A1 | 10/2005 |
| WO | 2006000904 A2 | 1/2006 |
| WO | 2006110783 A | 10/2006 |
| WO | 2006121557 A1 | 11/2006 |
| WO | 2006122255 A1 | 11/2006 |
| WO | 2006122258 A1 | 11/2006 |
| WO | 2006122259 A1 | 11/2006 |
| WO | 2006136087 A1 | 12/2006 |
| WO | 2007035789 A1 | 3/2007 |
| WO | 2007035790 A2 | 3/2007 |
| WO | 2007139933 A2 | 12/2007 |
| WO | 2007143113 A2 | 12/2007 |
| WO | 2007143152 A2 | 12/2007 |
| WO | 2008007145 A2 | 1/2008 |
| WO | 2009044803 A | 4/2009 |
| WO | 2009081208 A | 7/2009 |

OTHER PUBLICATIONS

International Search Report (dated Mar. 3, 2010); Written Opinion (dated Mar. 3, 2010); International Preliminary Report on Patentability (dated Sep. 1, 2010).
Felluga F et al., "A facile Chemoenzymatic Approach to Chiral Non-Racemic beta-alkyl-gamma-amino acids and 2-alkylsuccinic acids. A concise synthesis of (S)-(+)-Pregabalin", TetraHedron Assymmetry, Pergamon Press Ltd., Oxford, GB, vol. 19, No. 8, May 1, 2008, p. 945-955.
Gotoh Hiroaki et al., "Diphenylprolinol Silyl Ether as Catalyst of an Asymmetric, Catalytic, and Direct Michael Reaction of Nitroalkanes with .alpha.,.beta.-Unsaturated Aldehydes", Organic Letters, American Chemical Society, US, vol. 9, No. 25, Jan. 1, 2007, p. 5307-5309.
Lin S et al., "Chiral HPLC Separations for Process Development of S-(+)-Isobutyl Gaba, A Potential Anti-Epileptic Agent" Journal of Liquid Chromatography and Related Technologies, Monticello, NY, US, vol. 19, No. 16, Jan. 1, 1996, p. 2699-2708.

(Continued)

Primary Examiner — Susan Hanley
(74) Attorney, Agent, or Firm — Jeffrey S. Melcher; Manelli Selter PLLC

(57) ABSTRACT

The present invention relates to processes for the preparation of 5-methyl-3-nitromethyl-hexanoic acid ester and its salts. Also disclosed are processes for the preparation of 5-methyl-3-nitromethyl-hexanoic acid salt and a process for the preparation of 3-(aminomethyl)-5-methylhexanoic acid. (S)-5-Methyl-3-nitromethyl-hexanoic acid or (R)-5-methyl-3-nitromethyl-hexanoic acid in enantioenriched form or enantiopure form as well as salts thereof, (S)-5-methyl-3-nitromethyl-hexanoic acid ester or (R)-5-methyl-3-nitromethyl-hexanoic acid ester in enantioenriched form or enantiopure form and a compound, namely Formula (XIII), in racemic form, enantioenriched form or enantiopure form are also disclosed.

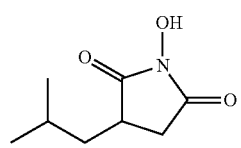

(XIII)

11 Claims, No Drawings

(56) References Cited

OTHER PUBLICATIONS

Felluga F et al., "A convenient chemoenzymatic synthesis of (R)-(−) and (S)-(+)-homo-beta-proline" Tetrahedron Asymmetry, Pergamon Press Ltd., Oxford, GB, vol. 15, No. 20, Oct. 18, 2004, p. 3323-3327.

Martinez C A et al., "Development of a Chemoenzymatic Manufacturing Process for Pregabalin" Organic Process Research and Development, vol. 12, No. 3, May 16, 2008, p. 392-398.

Ivancic Mirela et al., "Inverting enantio selectivity of *Burkholderia gladioli* esterase EstB by directed and designed evolution" Journal of Biotechnology, vol. 129, No. 1, Mar. 2007, p. 109-122.

Reiter B et al., "Cloning and Characterization of EstC from *Burkholderia gladioli*, a novel-type esterase related to plant enzymes", Applied Microbiology and Biotechnology, Springer Verlag, Berlin, DE, vol. 54, No. 6, Dec. 1, 2000, p. 778-785.

Petersen Evamaria I et al., "A novel esterase from *Burkholderia gladioli* which shows high deacetylation activity on cephalosporins is related to beta-lactamases and DD-peptidases", Journal of Biotechnology, vol. 89, No. 1, Jul. 26, 2001, p. 11-25.

Hoekstra M. S. et al., Chemical Development of CI-1008, an Enantiomerically Pure Anticonvulsant, Org. Proc. & Res. Dev. 1997, 1, p. 26-38.

Ooi, T.; Fujioka, S.; Maruoka, K., Highly Enantioselective Conjugate Addition of Nitroalkanes to Alkylidenemalonates Using Efficient Phase-Transfer Catalysis of N-Spiro Chiral Ammonium Bromides, J. Am. Chem. Soc, 2004, 126, 11790-11791.

Andruszkiewicz, R.; Silverman, R. B., A Convenient Synthesis of 3-Alkyl-4-aminobutanoic Acids, Synthesis Communications, Dec. 1989, 953-955.

K. M. Koeller and C-H. Wong, "Enzymes for chemical synthesis", Nature, 409: 232-240, 2001.

Wagner, U. G.; Petersen, E. I.; Schwab, EstB from *Burkholderia gladioli*: A novel esterase with a B-lactamase fold reveals steric factors to discriminate between esterolytic and B-lactam cleaving activity, Protein Sci. 2002, 11, 467-478.

Needleman, S. B. and Wunsch, C. D., A General Method Applicable to the Search for Similarities in the Amino Acid Sequence of Two Proteins, (1970), Journal of Molecular Biology, 48, 443-453.

Martin, The Preparation of 2-Heptenal and 2-Nonenal, J. Am. Chem. Soc. 1948, 70, 2601.

List, A Practical, Efficient, and Atom Economic Alternative to the Wittig and Horner-Wadsworth-Emmons Reactions for the Synthesis of (E)-alpha,beta-unsaturated Esters from Aldehydes, Tetrahedron 2006, 62, 476-482.

Bernard, Mechanism of Decarbalkoxylation of Arylmethylene-Propanedioic Acid Dimethyl Esters, Tetrahedron 1990, 46, 3929-3940.

Leonard, The Synthesis of Pyrrolizidines. VI. Stereochemical Correlation of 1-Methyl- and 1-Hydroxymethylpyrrolizidine Isomers with Certain Alkaloid Products, J. Am. Chem. Soc. 1950, 72, 2537-2542.

Pollini, Tetramethylguanidine-Catalyzed Addition of Nitro-methane to alpha,beta-Unsaturated Carboxylic Acid Esters, Synthesis Communications, 1972, 44-45.

Lampe, (Imidazolylphenyl) pyrrol-2-one Inhibitors of Cardiac cAMP Phosphodiesterase, J. Med. Chem. 1993, 36, 1041-1047.

Okino, Enantio- and Diastereoselective Michael reaction of 1,3-Dicarbonly Compounds to Nitroolefins Catalyzed by a Bifunctional Thiourea, J. Am. Chem. Soc. 2005, 127, 119-125.

\* cited by examiner

PROCESS FOR THE STEREOSELECTIVE ENZYMATIC HYDROLYSIS OF 5-METHYL-3-NITROMETHYL-HEXANOIC ACID ESTER

CROSS-REFERENCE TO RELATED APPLICATIONS

This application is a national stage entry under 35 U.S.C. 371 of International Application No. PCT/EP2009/056099, filed 19 May 2009, designating the United States. This application claims domestic priority under 35 U.S.C. 120 and 365 to U.S. Provisional Application No. 61/128,371, filed 21 May 2008. The complete contents of these applications are incorporated herein by reference.

FIELD OF THE INVENTION

The present invention relates to a process for the stereoselective enzymatic hydrolysis of 5-methyl-3-nitromethyl-hexanoic acid ester. A process for the preparation of 5-methyl-3-nitromethyl-hexanoic acid ester is also disclosed as well as processes for the preparation of 5-methyl-3-nitromethyl-hexanoic acid salt and 3-(aminomethyl)-5-methylhexanoic acid. (S)-5-Methyl-3-nitromethyl-hexanoic acid or (R)-5-methyl-3-nitromethyl-hexanoic acid in enantioenriched form or enantiopure form as well as salts thereof, (S)-5-methyl-3-nitromethyl-hexanoic acid ester or (R)-5-methyl-3-nitromethyl-hexanoic acid ester in enantioenriched form or enantiopure form and a compound, namely

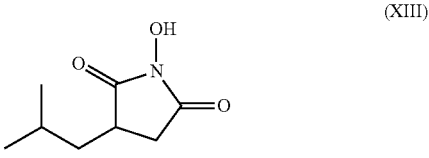

(XIII)

in racemic form, enantioenriched form or enantiopure form are also disclosed.

BACKGROUND OF THE INVENTION (S)-3-(Aminomethyl)-5-methylhexanoic acid (pregabalin, compound (I)) was first disclosed in EP-A-641330 and is currently being marketed under the trade name Lyrica® as an agent in anticonvulsant therapy. In EP-A-641330 a route for the synthesis of this compound is described. However, the disclosed process to this compound is lengthy (>10 steps), has a low efficiency, and uses pyrophoric or expensive reagents, such as butyl lithium and (+)-4-methyl-5- phenyl-2-oxazolidinone, respectively, which limits its use on an industrial scale.

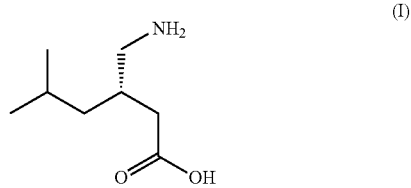

(I)

Structure of pregabalin (I)

In Hoekstra M. S. et al., *Org. Proc. & Res. Dev.* 1997, 1, 26-38 several routes to pregabalin are described. Two processes of particular economic interest are disclosed in EP-A-828704 and EP-A-830338, respectively. In the '704 patent application, 3-isobutyl glutaric acid, prepared from isovaleraldehyde and ethyl cyanoacetate, serves as a key intermediate, which is transformed via the corresponding cyclic anhydride to an amide which can be resolved in a classical manner with enantiopure phenylethylamine as the resolving agent (scheme 1). The amide is further subjected to a Hoffmann degradation leading to (S)-pregabalin. Improvements and variations of this process have been disclosed in WO 2006/122255, WO 2006/122258, WO 2006/122259, WO 2006/136087, WO 2007/035789, WO 2007/035790, and WO 2007/139933.

Scheme 1. Synthesis of pregabalin (I) according to EP-A-828704.

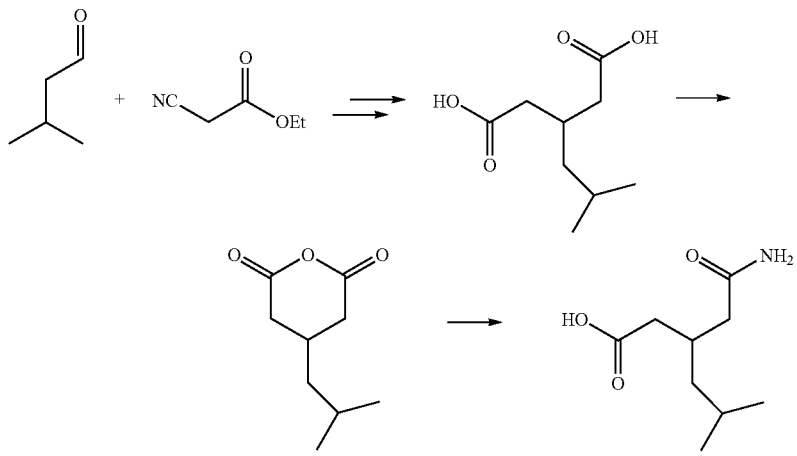

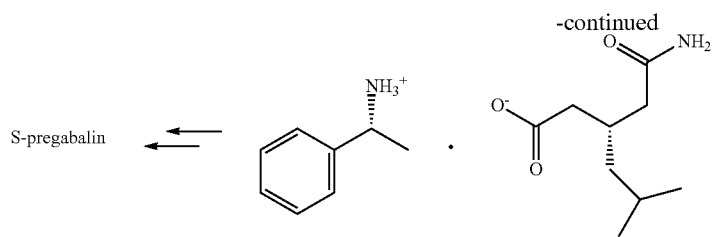

In EP-A-830338 racemic 3-(aminomethyl)-5-methylhexanoic acid is prepared and the racemate is resolved by (S)-mandelic acid as a chiral resolution agent. The racemic starting material is prepared in five steps from isovaleraldehyde and diethylmalonate. The resolution of a racemate at the end makes the synthesis costly and inefficient because the undesired isomer has to be taken along the whole process (Scheme 2). A variation of this process with the resolution prior to the reduction of the cyano group was disclosed in WO 2007/143152. Both processes suffer from disadvantages such as lengthy synthesis and low overall yield.

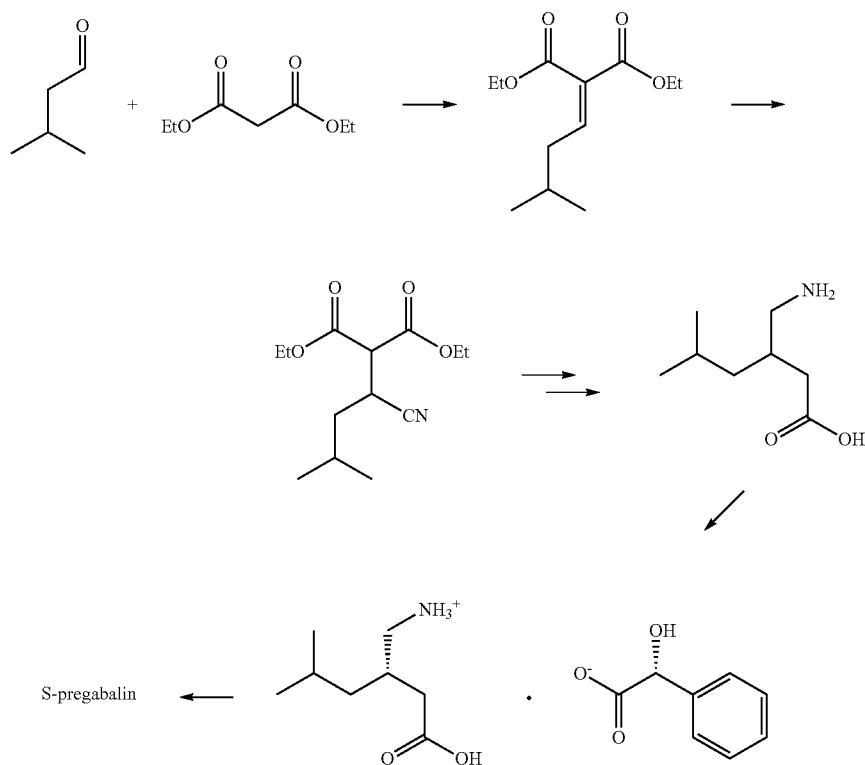

An asymmetric synthesis of an intermediate en route to pregabalin comprising a homogeneous catalytic hydrogenation with chiral phosphine-based ligands was disclosed in WO 2001/55090 and WO 2005/087370. The starting material is prepared in three steps which include the use of carbon monoxide which is a hazardous reagent and Pd which is an expensive catalyst.

Scheme 3. Synthesis of pregabalin (I) according to WO 2001/55090 and WO 2005/087370.

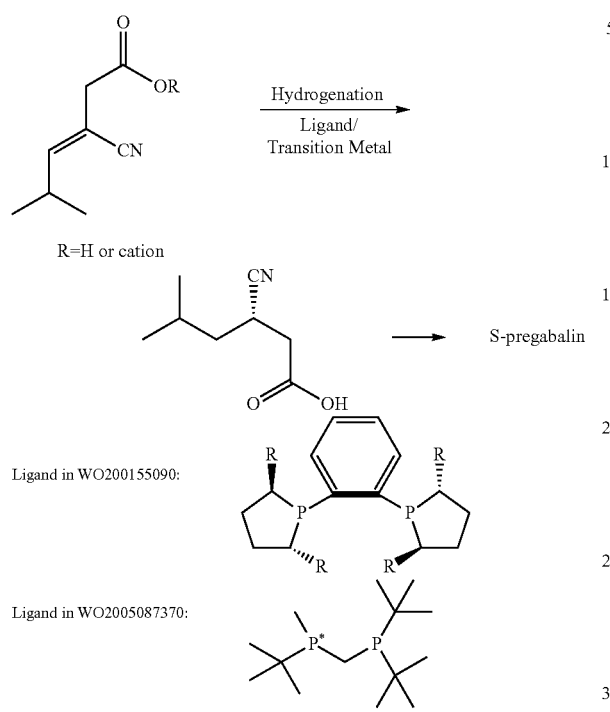

In WO 2006/110783 the conversion of chiral 2-(3-methyl-1-nitromethyl-butyl)-malonic acid dialkyl ester to pregabalin using a reduction-decarboxylation strategy was described. The sequence follows a prior art reaction sequence which has been applied to the synthesis, e.g. of baclofen (Ooi, T.; Fujioka, S.; Maruoka, K. *J. Am. Chem. Soc.*, 2005, 127, 119-125).

Purification processes leading to pregabalin which is free of some process-related impurities are described in WO 2006/122255 and WO 2006/121557.

All of above described processes make use of chiral auxiliaries, catalysts or additives. Such compound are usually hard to remove and are present in not desirable quantities in the final product.

Enzymatic kinetic resolutions of two nitrile-containing pregabalin precursors (compounds (II) and (III)) have been disclosed in WO 2005/100580 and WO 2006/00904. These two routes describe syntheses of pregabalin which have the disadvantage of using potassium cyanide, the handling of which can be problematic at an industrial scale due to safety reasons. In WO 2007/143113 an enzymatic kinetic resolution via hydrolysis or esterification of four substrates ((IV) and (V); R=H and Et, respectively) is described. However, no experimental details such as selectivity and yields are given.

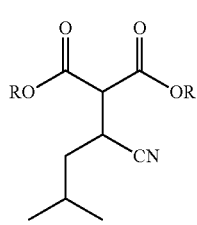

II

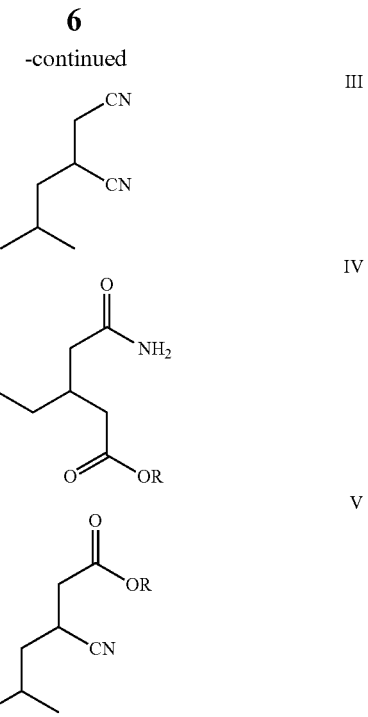

Structures of compounds which have been subjected to an enzymatic resolution

The synthesis of racemic pregabalin is described in Andruszkiewicz, R.; Silverman, R. B., *Synthesis* 1989, 953-955. The synthesis starts from (E)-5-methyl-hex-2-enoic acid ethyl ester, which is converted into 5-methyl-3-nitromethyl-hexanoic acid ethyl ester by a conjugate addition of nitromethane. This compound is converted into racemic pregabalin by catalytic hydrogenation followed by saponification.

Scheme 4. Synthesis of racemic pregabalin (I) according to Andruszkiewicz et al.

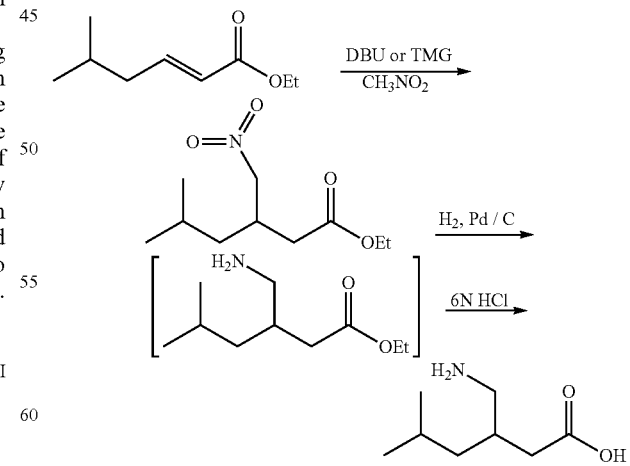

Recently, an enzymatic hydrolysis of 5-methyl-3-nitromethyl-hexanoic acid ethyl ester, prepared as described in Andruszkiewicz et al., has been described (Felluga, F. et al. Tetrahedron Asymmetry 2008, 19, 945-955, published online on May 6, 2008). The process described therein uses a particular enzyme, namely Novozyme 435, leading the enantiomerically enriched (S)-5-methyl-3-nitromethyl-hexanoic acid and enantiomerically enriched (R)-5-methyl-3-nitromethyl-hexanoic acid ethyl ester. Good selectivities only can be obtained, if the conversions are below 30% or above 60%, respectively, thus significantly limiting the yields. For the preparation of pregabalin the conversions have to be stopped at <30% in order to obtain (S)-5-methyl-3-nitromethyl-hexanoic acid in the desired quality, which can be further transformed into pregabalin. Higher conversion inevitably led to the formation of byproducts due to occurrence of Nef-type reactions.

Although some processes for the synthesis of pregabalin are available, further improvements in terms of using environmentally benign reagents, of reducing the number of isolated intermediates, and of increasing the overall yield would be highly desirable. Of particular interest are enzymatic methods, which allow the synthesis of (S)-5-methyl-3-nitromethyl-hexanoic acid in yields higher than 30%. Additionally, enzymes which allow the synthesis of (S)-5-methyl-3-nitromethyl-hexanoic acid esters by hydrolyzing the corresponding (R)-5-methyl-3-nitromethyl-hexanoic acid ester are highly desirable.

Additionally, processes which do not make use of chiral auxiliaries or chiral additives, which may be an harmful impurity in the final product, are highly desirable.

SUMMARY OF THE INVENTION

Processes for the preparation of 5-methyl-3-nitromethyl-hexanoic acid ester and its salts are disclosed. In addition, processes for the preparation of 5-methyl-3-nitromethyl-hexanoic acid salt and for the preparation of 3-(aminomethyl)-5-methylhexanoic acid are disclosed. (S)-5-Methyl-3-nitromethyl-hexanoic acid or (R)-5-methyl-3-nitromethyl-hexanoic acid in enantioenriched form or enantiopure form as well as salts thereof, (S)-5-methyl-3-nitromethyl-hexanoic acid ester or (R)-5-methyl-3-nitromethyl-hexanoic acid ester in enantioenriched form or enantiopure form and a compound, namely

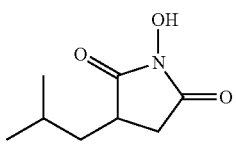

(XIII)

in racemic form, enantioenriched form or enantiopure form are also disclosed.

DETAILED DESCRIPTION OF THE INVENTION

The stereoselective enzymatic hydrolysis of 5-methyl-3-nitromethyl-hexanoic acid ester (VIII) can be carried out by contacting racemic 5-methyl-3-nitromethyl-hexanoic acid ester (VIII)

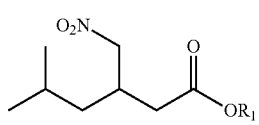

(VIII)

with an enzyme to render the (S)- or (R)-enantiomer of 5-methyl-3-nitromethyl-hexanoic acid ester (VIII) and a 5-methyl-3-nitromethyl-hexanoic acid salt having the other stereoconfiguration.

In the above formula $R_1$ can be an alkyl, an aryl or an arylalkyl group. The "alkyl" group can be a monovalent saturated hydrocarbon group, which may be straight chained or branched, or can include cyclic groups. Preferably, $R_1$ is straight chained or branched. Although the alkyl group may optionally include one or more heteroatoms N, O, S in its carbon skeleton, this is not preferred. The alkyl group may optionally be substituted, for example by halogen, hydroxy-, $C_{1-6}$-alkoxy-, or $C_{1-10}$-aryl-groups. Preferred examples of the alkyl group are hydrocarbon groups having 1 to 8 carbon atoms, such as methyl, ethyl, n-propyl, i-propyl, n-butyl, i-butyl, tert-butyl, n-pentyl, cyclopentyl, and cyclohexyl.

The "aryl" group can be a monovalent aromatic hydrocarbon, which may optionally include one or more heteroatoms N, O, or S in its ring. The aryl group can be optionally substituted, for example by halogen, hydroxy-, $C_{1-6}$-alkoxy-groups. Preferably, the aryl group has 6 to 10 carbon atoms. Examples of preferred aryl groups are phenyl, naphthyl, and phenathrenyl groups.

"Arylalkyl" groups are groups consisting of covalently linked aryl and alkyl groups, wherein the alkyl group is attached to the rest of the molecule. The aryl and alkyl moieties of the arylalkyl group are as defined above. Preferably, the arylalkyl group is benzyl or substituted benzyl such as $C_1$ alkyl-benzyl.

Of the $R_1$ groups mentioned above, ethyl is especially preferred.

In the stereoselective enzymatic hydrolysis racemic 5-methyl-3-nitromethyl-hexanoic acid ester (VIII) is contacted with an enzyme. The reaction products will differ depending on the selected enzyme.

In one method, the racemic 5-methyl-3-nitromethyl-hexanoic acid ester (VIII) can be converted into a mixture of (S)-5-methyl-3-nitromethyl-hexanoic acid ester S-(VIII) and (R)-5-methyl-3-nitromethyl-hexanoic acid salt R-(IX).

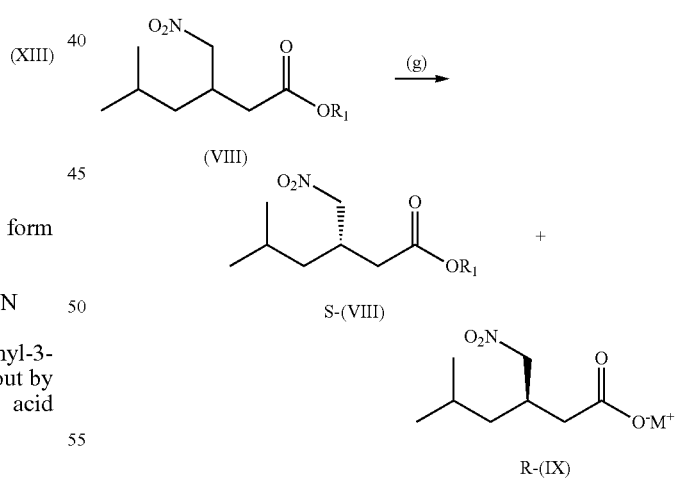

In another method, racemic 5-methyl-3-nitromethyl-hexanoic acid ester (VIII) can be converted into a mixture of (R)-5-methyl-3-nitromethyl-hexanoic acid ester R-(VIII) and (S)-5-methyl-3-nitromethyl-hexanoic acid salt S-(IX).

The cation $M^+$ of the salt is can be any suitable cation such as an alkali or alkaline earth cation. It will be typically determined by the conditions under which the reaction is conducted and will, in particular, correspond to the cation of the base which is usually employed.

Various screening methods can be used to identify an enzyme which is suitable for the stereoselective enzymatic hydrolysis of racemic 5-methyl-3-nitromethyl-hexanoic acid ester (VIII). Suitable enzymes can be identified by screening available enzymes, e.g. using high throughput screening techniques or by using enrichment isolation techniques. In such enrichment isolation techniques carbon-limited or nitrogen-limited media can be supplemented with an enrichment substrate, which is typically racemic 5-methyl-3-nitromethyl-hexanoic acid ester (VIII). Suitable microorganisms can be identified by a similar technique in which their ability to grow on media containing the enrichment substrate is evaluated. After this pre-selection step, the microorganisms giving the best results can be identified by contacting suspensions of those microorganisms with racemic 5-methyl-3-nitromethyl-hexanoic acid ester (VIII) and determining which microorganisms provide the greatest yields of desired reaction products (S)-5-methyl-3-nitromethyl-hexanoic acid ester S-(VIII) and (R)-5-methyl-3-nitromethyl-hexanoic acid salt R-(IX) or (R)-5-methyl-3-nitromethyl-hexanoic acid ester R-(VIII) and (S)-5-methyl-3-nitromethyl-hexanoic acid salt S-(IX), respectively.

The properties of the enzymes and microorganisms, which have been found to be effective, can be further enhanced by enzyme engineering. For example, enzyme engineering can be employed to improve the reaction rate, the yield and the selectivity of the reaction, in particular the enantioselectivity. Furthermore, enzyme engineering can be used to broaden the pH and temperature range at which the enzymes can be employed as well as their tolerance to certain solvents. Enzyme engineering techniques which can be employed include rational design methods, such as site-directed mutagenesis and in vitro-directed evolution techniques. Such techniques are described, e.g. in K. M. Koeller and C.-H. Wong, "Enzymes for chemical synthesis", *Nature*, 409: 232-240 and the references cited therein, which are incorporated herein by reference.

The enzyme can be used in the form of a crude lysate or in a purified form. Alternatively, the enzyme may be in the form of whole microbial cells, permeabilized microbial cells, extracts of microbial cells, partially purified enzymes, purified enzymes, and the like. Preferably, the enzyme is used in the form of crude lysate or lyophilisate.

Alternatively, the enzyme can be immobilized and used as such. Immobilization techniques are known to a person skilled in the art. Useful solid supports include, e.g., polymer matrices such as calcium alginate, polyacrylamide, Eupergit®, and other polymeric materials, as well as inorganic matrices, such as Celite®. Immobilization techniques are advantageous because the enzyme and the product can be easily separated. Additionally, the immobilized enzyme may be recycled and reused rendering the process more economic. Other techniques such as cross-linked enzyme aggregates (CLEAs) or cross-linked enzyme crystals (CLECs) are also applicable in the present invention.

Certain enzymes which have been found to be suitable for use in the present invention include lipases and esterases. Suitable enzymes include hydrolases as defined by class 3 of the ENZYME database (Bairoch A. *The ENZYME database in* 2000; Nucleic Acids Res 28:304-305 (2000); see also http://us.expasy.org/enzyme/). Preferred enzymes are hydrolases which are known to act on ester bonds (subclass 3.1 of the ENZYME database). Within this subclass, enzymes described as esterases and lipases are preferred. Examples of suitable enzymes include lipase B from *Candida antarctica*, esterase from hog liver, lipase C from *Candida antarctica*, lipase A from *Candida antarctica*, and esterase from pig liver (ICR-123, BioCatalytics/Codexis). These all gave a conversion of more than 50% of racemic 5-methyl-3-nitromethyl-hexanoic acid ester (VIII) to 5-methyl-3-nitromethyl-hexanoic acid salt (IX) in the stereoselective enzymatic hydrolysis reaction. These enzymes are available from Sigma-Aldrich (St. Louis, Mo.), Fluke (Buchs, Switzerland), Amano (Nagoya, Japan), Novo Nordisk (Bagsvaerd, Denmark), or from Technical University of Graz. Using these enzymes, the enantiomeric excess of the remaining enantiomer of 5-methyl-3-nitromethyl-hexanoic acid ester (VIII) was less than 80% ee at a conversion of 50%.

In addition, esterase EstB from *Burkholderia gladioli* (Wagner, U. G.; Petersen, E. I.; Schwab, H. *Prot. Sci.* 2002, 11, 467-478) and esterase EstC from *Burkholderia gladioli* (Reiter, B.; Glieder, A.; Talker, D.; Schwab, H. *Appl. Microbiol. Biotechnol.* 2000, 54, 778-785) are also suitable. EstB from *Burkholderia gladioli* preferentially hydrolyses the (R)-enantiomer of 5-methyl-3-nitromethyl-hexanoic acid ester R-(VIII), while EstC from *Burkholderia gladioli* preferentially hydrolyses the (S)-enantiomer of 5-methyl-3-nitromethyl-hexanoic acid ester (VIII). These esterases were provided by the Technical University of Graz, Austria.

The esterases EstB and EstC from *Burkholderia gladioli* can be recombinantly expressed in *E. coli* using standard cloning and expression methods. The obtained cell pellet is isolated by centrifugation of the fermentation broth. The cells can be disrupted by homogenization or any other technique. For further work up the homogenized cells can be subjected to flocculants like Sedipur® from BTC (BASF group). Additionally, the crude lysate can be concentrated using ultrafiltration to a factor between 5 and 25. This concentrated cell lysate can be used as is, lyophilized or used for any kind of immobilization.

The downstream process of the esterase can be tracked using the standard substrate p-nitrophenyl acetate for esterases. Esterases are catalyzing the hydrolysis of p-nitrophenyl acetate into p-nitrophenol and acetic acid. In this test the activity is determined by measuring the increase of absorption of p-nitrophenol (yellow, 404 nm) depending on the time.

The enantiomeric excess (ee) of the remaining 5-methyl-3-nitromethyl-hexanoic acid ester (VIII) or the formed 5-methyl-3-nitromethyl-hexanoic acid salt (IX) at a conversion of 50% was greater than 80% in every case. Depending on the reaction conditions (conversion, temperature, pH) ee-values of the remaining 5-methyl-3-nitromethyl-hexanoic acid ester (VIII) of up to 99% can be achieved.

For purposes of the present disclosure the term "enantiopure" means an enantiomeric ratio of R/S or S/R of more than 97.5/2.5, which corresponds to an ee value of >95%.

For purposes of the present disclosure the term "enantiomerically enriched" means an enantiomeric ratio of R/S or S/R of more than 75/25, which corresponds to an ee value of >50%.

Any suitable conditions for conducting the stereoselective enzymatic hydrolysis can be used. These will typically depend on the selected enzyme. Preferably, the reaction is performed in such a way that the ee of the remaining enantiomer of 5-methyl-3-nitromethyl-hexanoic acid ester (VIII) or the ee of the formed 5-methyl-3-nitromethyl-hexanoic acid salt (IX) are 50% or more, more preferably 80% or more, most preferably 90% or more.

The stereoselective enzymatic hydrolysis can be carried out in an aqueous system such as a solution, suspension or emulsion. The reaction mixture may comprise a single or multiple phases, and e.g. be a two- or three-phase system.

Examples of such two- or three-phase systems are described, e.g., on page 30, lines 14 to 33 in WO 2006/000904.

In a preferred embodiment the reaction is carried out in an aqueous solvent such as water or a mixture of water and an organic solvent such as ethanol, which is miscible therewith. Preferably, the aqueous solvent is water. Since the 5-methyl-3-nitromethyl-hexanoic acid ester (VIII) is only slightly soluble in water the reaction system is usually heterogeneous.

It was surprisingly found that the stereoselectivity of the enzymatic hydrolysis of 5-methyl-3-nitromethyl-hexanoic acid ester (VIII) can be advantageously enhanced by using methanol as co-solvent in an aqueous system according to the present invention. Enzymatic hydrolysis performed with enzyme EstC from *Burkholderia gladioli* in the presence of methanol revealed an unexpected increase in the stereoselectivity of the enzymatic hydrolysis of 5-methyl-3-nitromethyl-hexanoic acid ester (VIII) and resulted in an enantiomeric excess (ee) of the 5-methyl-3-nitromethyl-hexanoic acid ester (VIII) of up to 98%; see Example 8b. Enzymatic hydrolysis performed in the absence of methanol resulted in enantiomeric excess (ee) of about 88% or below; see, e.g. Example 8a.

Therefore, in another preferred embodiment, the stereoselective enzymatic hydrolysis is carried out in an aqueous system comprising methanol. Preferably, the aqueous system is an aqueous solution. Preferably, methanol is comprised in the aqueous system in the concentration of about 0.01% to about 5% [v/v], more preferably in the concentration of about 1% to about 3,5% [v/v], even more preferably in the concentration of about 1.5% to about 2.5% [v/v] and most preferably in the concentration of about 2.5% [v/v]. Preferably, the stereoselective enzymatic hydrolysis is carried out in a buffered mixture of water and methanol.

In a more preferred embodiment, the enzyme used in combination with methanol in accordance with the present invention is esterase EstC from *Burkholderia gladioli* or an esterase comprising an amino acid sequence having at least 50% identity to the amino acid sequence of EstC from *Burkholderia gladioli*, preferably at least 60% identity, more preferably at least 70% identity, even more preferably at least <75% identity, even more preferably at least 80% identity, more preferably at least 90% identity and even more preferably at least 95% identity, even more preferably at least 97% identity, even more preferably at least 99% identity and most preferably exact identity to the amino acid sequence of EstC from *Burkholderia gladioli*.

The amino acid sequence identity referred to herein is determined as the degree of identity between the two sequences indicating a derivation of the first sequence from the second. The identity may be suitably determined by means of computer programs in the art such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-453. Using GAP with the following settings for the polypeptide sequence comparison: GAP creation penalty of 3.0 and GAP extension penalty of 0.1, the mature part of a esterase amino acid sequence of the invention exhibits a degree of identity of at least 50% identity to the amino acid sequence of EstC from *Burkholderia gladioli*, preferably at least 60% identity, more preferably at least 70% identity, even more preferably at least <75% identity, even more preferably at least 80% identity, more preferably at least 90% identity and even more preferably at least 95% identity, even more preferably at least 97% identity, even more preferably at least 99% identity with the mature part of the amino acid sequence of EstC from *Burkholderia gladioli* from position 1 to 298 (in BASBPN numbering). Accordingly, the identity will be defined as the number of identical residues divided by 298.

The present invention relates to a process for stereoselective enzymatic hydrolysis of chiral esters, which are substrates of EstC from *Burkholderia gladioli*, in the presence of methanol, wherein the chiral esters have a chiral or prochiral center in the acid moiety in proximity to carbonyl group. Preferably, the chiral center is in α, β or γ position to carbonyl carbon, more preferably in α or β position. The acid moiety of the chiral ester can be $C_{3-15}$ alkyl, linear or branched, optionally substituted with one or more —CN, -halogen, —$NO_2$, —$N_3$, —OH, —SH, —$NH_2$, —NHR, —$NR_2$, —OR or —SR, wherein R is $C_{1-6}$ alkyl or $C_{1-6}$ alkanoyl; $C_{6-10}$ aryl or substituted aryl, unsaturated or saturated heteroaryl or substituted heteroaryl comprising more or more heteratoms.

The alcohol moiety ROH can be selected from R=$C_{1-6}$ linear or branched alkyl; preferentially from MeOH, EtOH, 2-propanol, or butanol; or $C_{1-10}$ aryl or substituted aryl.

The stereoselective enzymatic hydrolysis of chiral esters in the presence of methanol can be conducted using EstC from *Burkholderia gladioli* or an esterase comprising an amino acid sequence having at least 50% identity to the amino acid sequence of EstC from *Burkholderia gladioli*, preferably at least 60% identity, more preferably at least 70% identity, even more preferably at least <75% identity, even more preferably at least 80% identity, more preferably at least 90% identity and even more preferably at least 95% identity, even more preferably at least 97% identity, even more preferably at least 99% identity and most preferably exact identity to the amino acid sequence of EstC from *Burkholderia gladioli*.

The stereoselective enzymatic hydrolysis of chiral esters in the presence of methanol can be conducted at any condition as described herein for the process of stereoselective enzymatic hydrolysis of 5-methyl-3-nitromethyl-hexanoic acid ester.

The stereoselective enzymatic hydrolysis can be conducted at any appropriate pH. Preferably, a pH ranging from about 5 to about 11, more preferably from about 6 to about 9.5 is chosen. The pH can be adjusted, e.g., by addition of a base such as an inorganic or an organic base. Examples of organic bases are triethylamine, diisopropylethylamine, trioctylamine. Preferably, an inorganic base, such as ammonium, alkali or alkaline earth hydroxides (e.g., $NH_4OH$, NaOH, KOH, LiOH) or ammonium, alkali or alkaline earth carbonates (e.g., $Na_2CO_3$, $K_2CO_3$, or $Li_2CO_3$), is added. The base can be added in solution, preferably as an aqueous solution. The concentration of this solution can vary from saturation to high dilution (e.g. about 0.01M). Preferably, the concentration of the base ranges from about 5M to about 10M.

If desired, the pH of the reaction medium can be buffered. Suitable buffers include ammonium, alkali or alkaline earth phosphates (e.g., ammonium phosphate, potassium phosphate and sodium phosphate) or ammonium, alkali or alkaline earth acetates (e.g., ammonium acetate and calcium acetate) or other buffers having a pKa of about 5 to about 10.

The temperature at which the stereoselective enzymatic hydrolysis can be conducted can vary in a wide range. For example, the temperature can range from about 0° C. to about 70° C. In a preferred embodiment the reaction temperature is from about 5° C. to about 30° C.

In order to get an high enantiomeric excess of the desired enantiomer, it can be preferable to stop the reaction after a certain conversion has been achieved. If the reaction is conducted to completion, then the corresponding racemic 5-methyl-3-nitromethyl-hexanoic acid salt (IX) is obtained. The most appropriate amount of conversion will depend on the chosen enzyme and can be determined by a person skilled in the art.

If esterase EstB from *Burkholderia gladioli* is employed, the reaction is preferably stopped at a conversion of about 50% to about 70%. More preferably, the reaction is stopped at a conversion of about 50% to about 55%. The reaction can be stopped by addition of an organic solvent. Preferentially a water immiscible organic solvent such as ethyl acetate can be added. The reaction can also be stopped by standard method known to a person skilled in the art such as temperature increase, addition of acid or base and the like.

If esterase EstC from *Burkholderia gladioli* is employed, the reaction is preferably stopped at a conversion of about 40% to about 50%. More preferably, the reaction is stopped at a conversion of about 45% to about 50%. The reaction can be stopped by addition of an organic solvent. Preferably, a water immiscible organic solvent such as ethyl acetate is added.

If *Candida Antarctica* B is employed, the reaction is preferably stopped at a conversion of about 40% to about 50%. More preferably, the reaction is stopped at a conversion of about 45% to about 50%. The reaction can be stopped by addition of an organic solvent. Preferably, a water immiscible organic solvent such as ethyl acetate is added. Preferably, the pH will be above 7.4.

The amount of conversion can be determined by any suitable method, such as by measuring the amount of consumed base or by HPLC measurements.

After or during the stereoselective enzymatic hydrolysis, the unreacted enantiomer of 5-methyl-3-nitromethyl-hexanoic acid ester (VIII) (for example, (S)-5-methyl-3-nitromethyl-hexanoic acid ester S-(VIII)) and the resultant enantiomer of 5-methyl-3-nitromethyl-hexanoic acid salt (IX) (for example, (R)-5-methyl-3-nitromethyl-hexanoic acid salt R-(IX)) can be separated using techniques known to a person skilled in the art. For instance, the unreacted enantiomer of 5-methyl-3-nitromethyl-hexanoic acid ester (VIII) can be removed from the reaction mixture by one or more extractions with an organic solvent, which is not miscible with water, such as ethyl acetate or heptane, so that the resultant enantiomer of 5-methyl-3-nitromethyl-hexanoic acid salt (IX) remains in the aqueous layer.

Optionally, the undesired enantiomer (e.g. in the case of pregabalin the R-enantiomer) can be submitted to a racemization process and recycled into the stereoselective enzymatic hydrolysis process.

Although the stereoselective enzymatic hydrolysis can be employed in a variety of processes it is particularly well suited for the preparation of enantioenriched or enantiopure 3-(aminomethyl)-5-methylhexanoic acid (I), in particular pregabalin.

Scheme 5 shows a complete reaction scheme for the preparation of (S)-3-(aminomethyl)-5-methylhexanoic acid (I) in which the claimed stereoselective enzymatic hydrolysis is employed (reaction (g)). As can be seen from the reaction scheme, the starting material racemic 5-methyl-3-nitromethyl-hexanoic acid ester rac-(VIII) can be prepared via various synthetic routes. Furthermore, the end product of the claimed reaction, namely the desired enantiomer of 5-methyl-3-nitromethyl-hexanoic acid ester (VIII), can be processed to the desired enantiomer of 3-(aminomethyl)-5-methylhexanoic acid (I) using various synthetic routes. These reactions, which are given as an illustration and are not exhaustive, will be described in the following. For the sake of simplicity the reactions are based on one of the two enantiomeric embodiments. However, it is clear that the reaction scheme can also be applied to the other enantiomer. Furthermore, although all of the intermediates are shown in Scheme 5 it is clear that they need not all be isolated before they are reacted further.

Scheme 5 Overview over the reactions discussed in the present application using an (R)-selective enzyme

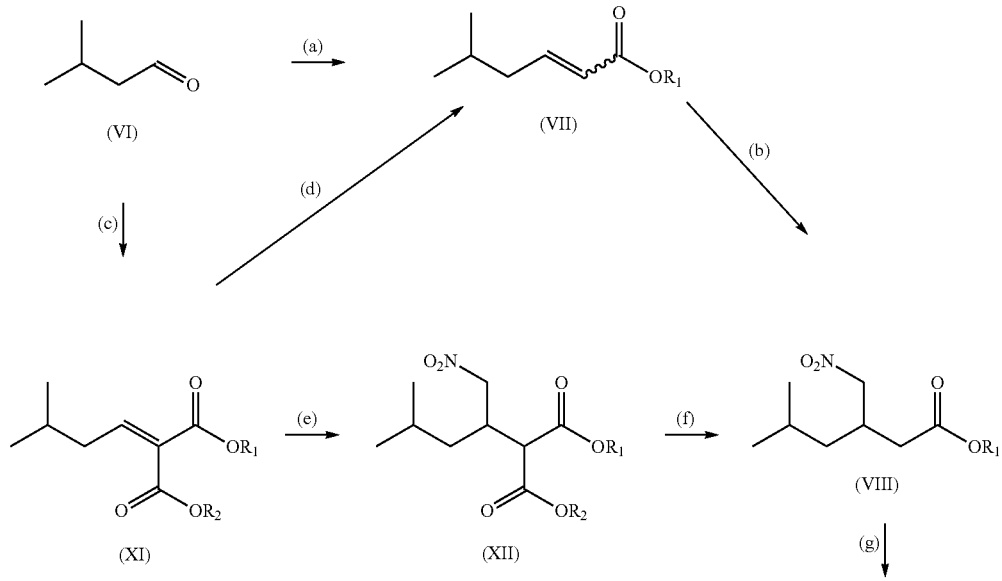

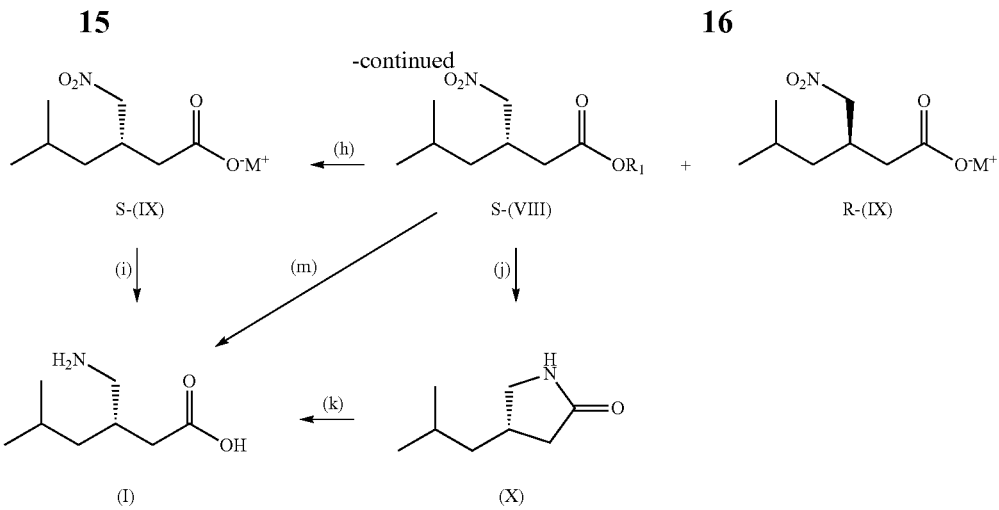

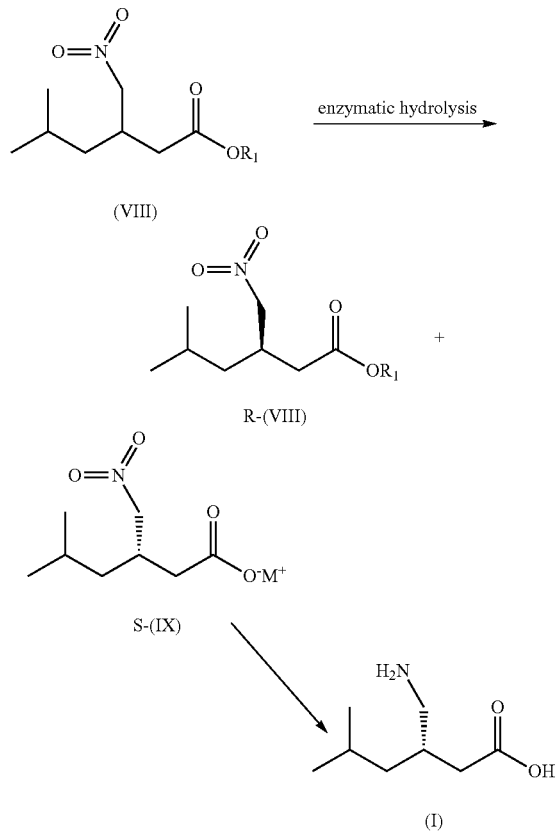

Scheme 6. Overview over the reactions discussed in the present application using an (S)-selective enzyme The processes shown in Scheme 5 and Scheme 6 are fast, economical, and simple and provide pregabalin in a high yield and high optical purity. A preferred process comprises the steps of a) and b) to obtain compound VIII. One preferred process for the preparation of compound I comprises the steps of sequentially carrying out reactions g), h), i) or g), j), k), respectively.

A further advantage is the early separation of the enantiomers. In prior art processes such as those described, e.g., in WO 2008/007145 or U.S. Pat. No. 5,637,767, the separation of the enantiomers takes place at the stage of racemic pregabalin. One main advantage of the present invention is that only half of the amount of an expensive transition metal catalyst is required for the last step because the undesired enantiomer is separated at an earlier stage and is therefore not subjected to the reduction.

An advantage of the process is that no chiral auxiliaries are needed for the preparation of the desired enantiomer of 3-(aminomethyl)-5-methylhexanoic acid (I). Such auxiliaries result in impurities in the final product.

For the purposes of this disclosure, a compound is considered to be racemic if it comprises the two possible enantiomers in a ratio of about 50:50. A compound is considered to be "substantially enantiopure" or "enantioenriched" if it comprises about 90% or more of only one enantiomer.

For the purposes of this disclosure a compound is considered to be "enantiomerically pure" if the content of one enantiomer is about 95% or more, preferably about 98% or more, more preferably about 99% or more.

For the purposes of this disclosure, a compound is considered to be "substantially free" of impurities if the respective impurity is present in an amount of about 3% or less, preferably about 1% or less, more preferably about 0.1% or less.

Reaction (a)

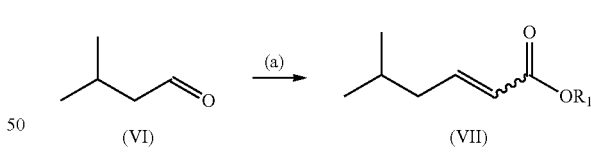

In reaction (a) 3-methylbutyraldehyde (VI) is converted to the 5-methyl-hex-2-enoic acid ester (VII). The wavy line in formula (VII) indicates that the double bond can either have the cis- or trans-orientation. Various synthetic routes can be chosen for this reaction.

In one method, 3-methylbutyraldehyde (VI) can be submitted to a Wittig-Horner reaction. One particular reaction of this type has been the focus of a recent patent application WO 2003/062185, which is incorporated herein by reference. According to this patent application, a Wittig-Horner reaction of 3-methylbutyraldehyde (VI) and a suitable phosphonate $(RO)_2P(=O)-CH_2-COOR_1$ (wherein R is an aliphatic $C_{1-3}$ moiety and $R_1$ is as defined above) is conducted in water at a distinct temperature in the presence of alkali carbonate. The yields obtained by this process are about 90%. A disadvantage of the process described in WO 2003/062185 is the use of the rather expensive phosphonate as a C$_2$-synthon.

In an alternative and preferred embodiment, 3-methylbutyraldehyde (VI) can be reacted with a monoalkylmalonate HOOC—CH$_2$—COOR$_1$ to give 5-methyl-hex-2-enoic acid ester (VII).

The reaction can be carried out with or preferably without a solvent. If desired, a catalytic amount of one or more bases can be added. For example, piperidine can be used as a first base in catalytic quantities (e.g., <0.05 eq. relative to 1 eq. of aldehyde VI) and pyridine can be used as a second base in about 1.0 to about 5.0 equivalents relative to 1 eq. of aldehyde VI. The reaction will be typically conducted at a temperature of 50° C. to 100° C. Other conditions for such a conversion, which can also be applied to the present invention, are described in: *Gazz. Chim. Ital.* 1953, 83, 1043-1045; or *J. Am. Chem. Soc.* 1948, 70, 2601; or *Tetrahedron* 2006, 62, 476-482.

5-Methyl-hex-2-enoic acid ester (VII) can be isolated or further processed without purification. Preferably, 5-methyl-hex-2-enoic acid ester (VII) is purified by extraction with an acid prior to conversion to 5-methyl-3-nitromethyl-hexanoic acid ester (VIII).
Reaction (b)

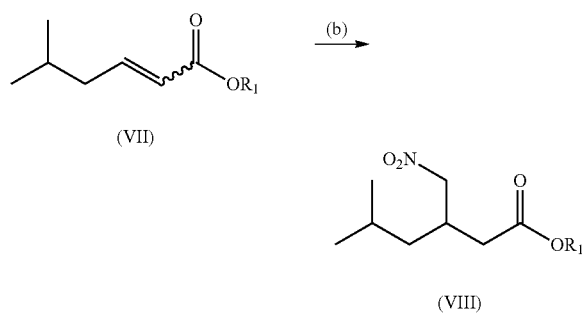

In this reaction R$_1$ is as defined above. 5-Methyl-hex-2-enoic acid ester (VII) can be converted into 5-methyl-3-nitromethyl-hexanoic acid ester (VIII) by addition of nitromethane. Preferably about 1 to about 5 equivalents of nitromethane CH$_3$NO$_2$, most preferably about 1.5 to about 2.5 eq. of nitromethane, relative to 1 eq. of 5-methyl-hex-2-enoic acid ester (VII), are used.

Reaction (b) can be carried out with or preferably without a solvent. If a solvent is employed, it can be selected from any protic or aprotic organic solvent. Preferred organic solvents are CH$_2$Cl$_2$, acetonitrile, ethanol, methanol, or tetrahydrofuran.

Reaction (b) can be carried out at various temperatures, for example at a temperature of about 0° C. to about 100° C.; preferably at a temperature of about 40° C. to about 60° C.

If desired, reaction (b) can be optionally conducted in the presence of a base. Any suitable base can be employed as long as it can deprotonate the acidic proton of nitromethyl group. The base can be an organic base such as a trialkylamine (wherein the alkyl group preferably has 1 to 4 carbon atoms), an alkoxide (such as sodium methoxide or sodium tert-butoxide), strong organic bases such as 1,8-diazabicyclo[5.4.0]undec-7-ene (DBU) or N,N,N',N'-tetramethylguanidine (TMG), or an inorganic base such as an ammonium, alkali or alkaline earth carbonate, an ammonium, alkali or alkaline earth hydroxide or an ammonium, alkali or alkaline earth hydrogencarbonate. Preferably, the conversion is carried out in the presence of a strong organic base such as 1,8-diazabicyclo[5.4.0]undec-7-ene (DBU) or N,N,N',N'-tetramethylguanidine (TMG). The amount of the base is not particularly limited. However, it will be typically added in substoichiometric quantities. For example, about 0.1 to about 0.5 eq. of base relative to 1 eq. of 5-methyl-hex-2-enoic acid ester (VII) are used.

5-Methyl-3-nitromethyl-hexanoic acid ester (VIII) is typically obtained in a yield of more than about 80%, more typically in a yield of more than about 90% in reaction (b).
Reaction (c)

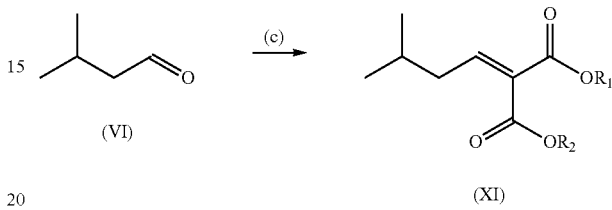

3-Methylbutyraldehyde (VI) can be converted into 2-(3-methyl-butylidene)-malonic acid diester (XI) by a Knoevenagel condensation reaction with dialkylmalonate R$_1$OOC—CH$_2$—COOR$_2$. In this reaction R$_1$ and R$_2$ can be the same or different and can have the meanings given for R$_1$ above. Preferably, reaction (c) is carried out in the presence of a base such as di-n-propylamine. Preferably, a stoichiometric amount or a slight excess of dialkylmalonate (about 1.0 to about 1.5 eq.) relative to 1 eq. of 3-methylbutyraldehyde (VI) is employed. It is also preferred to employ stoichiometric or substoichiometric quantities of amine (about 1.0 eq. or less) relative to 1 eq. of 3-methylbutyraldehyde (VI). The synthesis of 2-(3-methyl-butylidene)-malonic acid diester (XI) using such a Knoevenagel condensation is described, e.g., in EP-A-830338.

If desired, 2-(3-methyl-butylidene)-malonic acid diester (XI) obtained in this reaction can be purified by methods known to a person skilled in the art before it is reacted further. However, 2-(3-methyl-butylidene)-malonic acid diester (XI) is preferably processed further without purification.
Reaction (d)

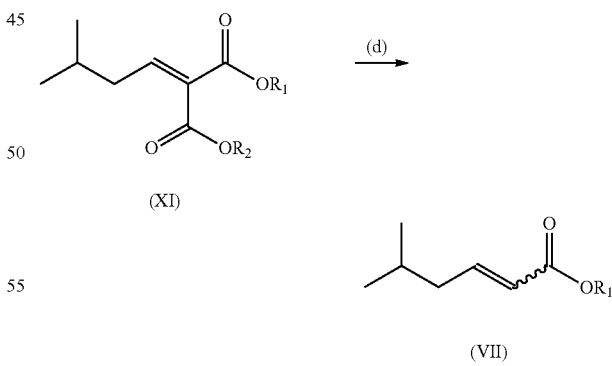

In this reaction R$_1$ and R$_2$ are as defined above.

2-(3-Methyl-butylidene)-malonic acid diester (XI) can be reacted to 5-methyl-hex-2-enoic acid ester (VII) by decarboxylation. The decarboxylation is preferably carried out at a temperature in the range of about 100° C. to about 180° C. in a suitable polar aprotic solvent (such as DMSO, or NMP). Optionally, a salt (such as NaCl, or LiCl) can be added in order to accelerate the decarboxlation. Other reaction conditions such as a different temperature, solvent, or additives are also applicable. Examples for such conditions using other substrates are described in Tetrahedron 1990, 46, 3929-3940.

Reaction (e)

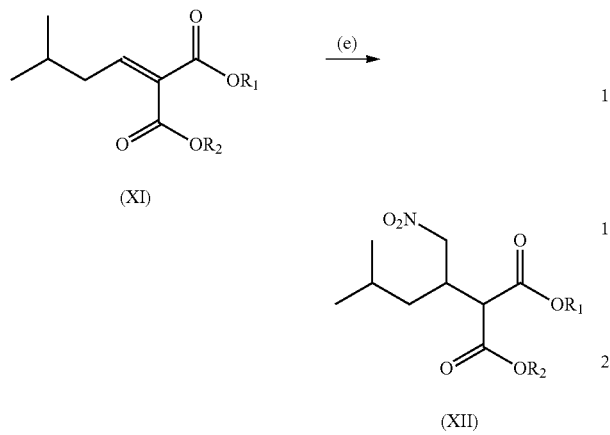

In this reaction $R_1$ and $R_2$ are as defined above.

2-(3-Methyl-butylidene)-malonic acid diester (XI) can be converted into 2-(3-methyl-1-nitromethyl-butyl)-malonic acid diester (XII) by addition of nitromethane.

Preferably, about 1 to about 5 equivalents of nitromethane $CH_3NO_2$, more preferably about 1.5 to about 2.5 eq. of nitromethane, relative to 1 eq. of 2-(3-methyl-butylidene)-malonic acid diester (XI), are used.

Reaction (e) can be carried out with or, more preferably, without a solvent. If a solvent is employed, it can be selected from the group consisting of any protic or aprotic organic solvent. Preferred organic solvents are $CH_2Cl_2$, acetonitrile, ethanol, methanol, or tetrahydrofuran.

Reaction (e) can be carried out at various temperatures, for example at a temperature of about 0° C. to about 100° C., preferably at a temperature of about 40° C. to about 60° C.

Reaction (e) can be optionally conducted in the presence of a base. Any suitable base can be employed as long as it can deprotonate the acidic proton of nitromethan. The base can be an organic base such as a trialkylamine (wherein the alkyl group preferably has 1 to 4 carbon atoms), an alkoxide (such as sodium methoxide or sodium tert-butoxide), strong organic bases such as 1,8-diazabicyclo[5.4.0]undec-7-ene (DBU) or N,N,N',N'-tetramethylguanidine (TMG), or an inorganic base such as an ammonium, alkali or alkaline earth carbonate, an ammonium, alkali or alkaline earth hydroxide or an ammonium, alkali or alkaline earth hydrogencarbonate. Preferably, the conversion is carried out in the presence of a strong organic base such as 1,8-diazabicyclo[5.4.0]undec-7-ene (DBU) or N,N,N',N'-tetramethylguanidine (TMG). The amount of the base is not particularly limited. However, it will be typically added in substoichiometric quantities. For example, about 0.1 to about 0.5 eq. of base relative to 1 eq. of 2-(3-methyl-butylidene)-malonic acid diester (XI) are used.

Typical conditions for the addition of nitromethane, which can also be applied in reaction (e), are described in *J. Am. Chem. Soc.* 1950, 72, 2537-2542; *Synthesis* 1972, 44-45; *J. Med. Chem.* 1993, 36, 1041-1047; or *Chem. Pharm. Bull.* 1995, 43, 1125-1131.

The yield of reaction (e) is usually above about 90%, preferably above about 95%.

Reaction (f)

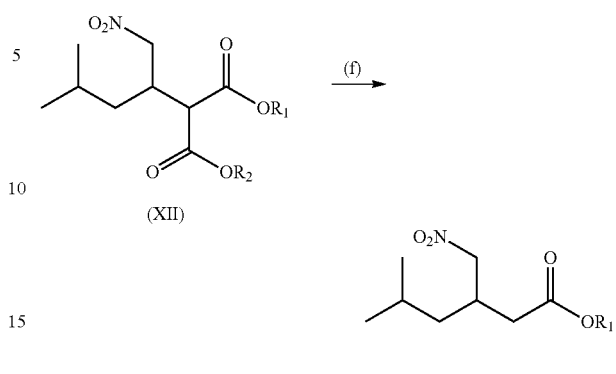

In this reaction $R_1$ and $R_2$ are as defined above.

2-(3-Methyl-1-nitromethyl-butyl)-malonic acid diester (XII) can be converted into 5-methyl-3-nitromethyl-hexanoic acid ester (VIII) by decarboxylation. The decarboxylation is preferably carried out at a temperature in the range of about 100° C. to about 200° C. in a suitable polar aprotic solvent such as DMSO or DMF. Optionally, a salt such as NaCl can be added in order to enhance the yield. Such a reaction is described, e.g., in WO 2006/110783.

Reaction (g)

Reaction (g) is one method for the stereoselective enzymatic hydrolysis described above. However, it should be understood that reaction (g) can equally apply to the other enantiomer.

In the stereoselective enzymatic hydrolysis racemic 5-methyl-3-nitromethyl-hexanoic acid ester (VIII) is contacted with an enzyme. The reaction products will differ depending on the selected enzyme.

In one method the racemic 5-methyl-3-nitromethyl-hexanoic acid ester (VIII) is prepared using reactions a) and b) as described above.

In one method the racemic 5-methyl-3-nitromethyl-hexanoic acid ester (VIII) is converted into a mixture of (S)-5-methyl-3-nitromethyl-hexanoic acid ester S-(VIII) and (R)-5-methyl-3-nitromethyl-hexanoic acid salt R-(IX).

In a method the racemic 5-methyl-3-nitromethyl-hexanoic acid ester (VIII) is converted into a mixture of (S)-5-methyl-3-nitromethyl-hexanoic acid ester S-(VIII) and (R)-5-methyl-3-nitromethyl-hexanoic acid salt R-(IX) by enzymatic hydrolysis at a pH of 8-14.

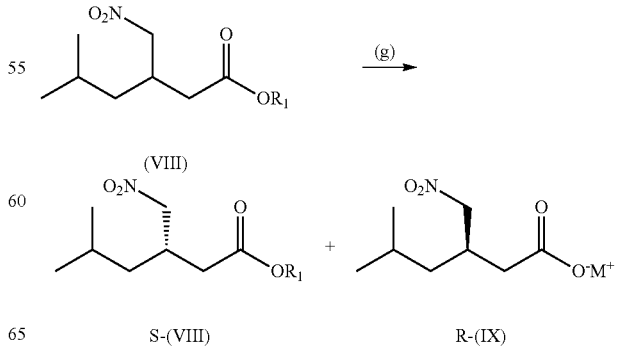

In a method, racemic 5-methyl-3-nitromethyl-hexanoic acid ester (VIII) is converted into a mixture of (R)-5-methyl-3-nitromethyl-hexanoic acid ester R-(VIII) and (S)-5-methyl-3-nitromethyl-hexanoic acid salt S-(IX).

Cation $M^+$ of the salt can be any suitable cation such as an alkali or alkaline earth cation. It will typically be determined by the conditions under which the reaction is conducted and will, in particular, correspond to the cation of the base which is usually employed.

The enzyme can be used in the form of a crude lysate or in a purified form. Alternatively, the enzyme may be in the form of whole microbial cells, permeabilized microbial cells, extracts of microbial cells, partially purified enzymes, purified enzymes, and the like. Preferably, the enzyme is used in the form of crude lysate or lyophilisate.

Alternatively, the enzyme can be immobilized and used as such. Immobilization techniques are known to a person skilled in the art. Useful solid supports include, e.g., polymer matrices such as calcium alginate, polyacrylamide, Eupergit®, and other polymeric materials, as well as inorganic matrices, such as Celite®. Immobilization techniques are advantageous because the enzyme and the product can be easily separated. Additionally, the immobilized enzyme may be recycled and reused rendering the process more economical. Other techniques such as cross-linked enzyme aggregates (CLEAs) or cross-linked enzyme crystals (CLECs) are also applicable in the present invention.

The enantiomeric excess (ee) of the remaining 5-methyl-3-nitromethyl-hexanoic acid ester (VIII) or the formed 5-methyl-3-nitromethyl-hexanoic acid salt (IX) at a conversion of 50% was greater than 80% in every case. Depending on the reaction conditions (conversion, temperature, pH) ee-values of the remaining 5-methyl-3-nitromethyl-hexanoic acid ester (VIII) of up to 99% can be achieved.

The conditions for conducting the stereoselective enzymatic hydrolysis will typically depend on the selected enzyme. Preferably, the reaction is performed in such a way that the ee of the remaining enantiomer of 5-methyl-3-nitromethyl-hexanoic acid ester (VIII) or the ee of the formed 5-methyl-3-nitromethyl-hexanoic acid salt (IX) are 50% or more, more preferably 80% or more, most preferably 90% or more.

The stereoselective enzymatic hydrolysis can be carried out in an aqueous system such as a solution, suspension or emulsion. The reaction mixture may comprise a single or multiple phases, and e.g. be a two- or three-phase system. Examples of such two- or three-phase systems are described, e.g., on page 30, lines 14 to 33 in WO 2006/000904.

In a preferred method the reaction is carried out in an aqueous solvent such as water or a mixture of water and an organic solvent such as ethanol, which is miscible therewith. Preferably, the aqueous solvent is water. Since the 5-methyl-3-nitromethyl-hexanoic acid ester (VIII) is only slightly soluble in water the reaction system is usually heterogeneous.

As described herein above, the stereoselectivity of the enzymatic hydrolysis of 5-methyl-3-nitromethyl-hexanoic acid ester (VIII) can be advantageously enhanced by using methanol as co-solvent in an aqueous system according to the present invention.

Therefore, in another preferred embodiment, the stereoselective enzymatic hydrolysis is carried out in an aqueous system comprising methanol. Preferably, the aqueous system is an aqueous solution. Preferentially, methanol is comprised in the aqueous system in the concentration of about 0.01% to about 5% [v/v], preferably in the concentration of about 1% to about 3,5% [v/v], more preferably in the concentration of about 1.5% to about 2.5% [v/v] and most preferably in the concentration of about 2.5% [v/v]. Preferably, the stereoselective enzymatic hydrolysis is carried out in a buffered mixture of water and methanol.

In a more preferred embodiment, the enzyme used in combination with methanol in accordance with the present invention is esterase EstC from *Burkholderia gladioli* or an esterase comprising an amino acid sequence having at least 50% identity to the amino acid sequence of EstC from *Burkholderia gladioli*, preferably at least 60% identity, more preferably at least 70% identity, even more preferably at least <75% identity, even more preferably at least 80% identity, more preferably at least 90% identity and even more preferably at least 95% identity, even more preferably at least 97% identity, even more preferably at least 99% identity and most preferably exact identity to the amino acid sequence of EstC from *Burkholderia gladioli*.

The amino acid sequence identity referred to above is determined as the degree of identity between the two sequences indicating a derivation of the first sequence from the second. The identity may be suitably determined by means of computer programs in the art such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-453. Using GAP with the following settings for the polypeptide sequence comparison: GAP creation penalty of 3.0 and GAP extension penalty of 0.1, the mature part of a esterase amino acid sequence of the invention exhibits a degree of identity of at least 50% identity to the amino acid sequence of EstC from *Burkholderia gladioli*, preferably at least 60% identity, more preferably at least 70% identity, even more preferably at least <75% identity, even more preferably at least 80% identity, more preferably at least 90% identity and even more preferably at least 95% identity, even more preferably at least 97% identity, even more preferably at least 99% identity with the mature part of the amino acid sequence of EstC from *Burkholderia gladioli* from position 1 to 298 (in BASBPN numbering). Accordingly, the identity will be defined as the number of identical residues divided by 298.

The stereoselective enzymatic hydrolysis can be conducted at any appropriate pH. Preferably, a pH ranging from about 5 to about 11, more preferably from about 6 to about 9.5, is chosen. The pH can be adjusted, e.g., by addition of a base such as an inorganic or an organic base. Examples of organic bases are triethylamine, diisopropylethylamine, trioctylamine. Preferably, an inorganic base, such as ammonium, alkali or alkaline earth hydroxides (e.g., $NH_4OH$, NaOH, KOH, LiOH) or ammonium, alkali or alkaline earth carbonates (e.g., $Na_2CO_3$, $K_2CO_3$, or $Li_2CO_3$), is added. The base can be added in solution, preferably as an aqueous solution. The concentration of this solution can vary from saturation to high dilution (e.g. about 0.01M). Preferably, the concentration of the base ranges from about 5M to about 10M.

If desired, the pH of the reaction medium can be buffered. Suitable buffers include ammonium, alkali or alkaline earth phosphates (e.g., ammonium phosphate, potassium phosphate and sodium phosphate) or ammonium, alkali or alkaline earth acetates (e.g., ammonium acetate and calcium acetate) or other buffers having a pKa of about 5 to about 10.

The temperature at which the stereoselective enzymatic hydrolysis can be conducted can vary in a wide range. For example, the temperature can range from about 0° C. to about 70° C. In a preferred embodiment the reaction temperature is from about 5° C. to about 30° C.

In order to get a suitably high enantiomeric excess of the desired enantiomer, it can be preferable to stop the reaction after a certain conversion has been achieved. If the reaction is conducted to completion, then the corresponding racemic 5-methyl-3-nitromethyl-hexanoic acid salt (IX) is obtained. The most appropriate amount of conversion will depend on the chosen enzyme and can be determined by a person skilled in the art.

If esterase EstB from *Burkholderia gladioli* is employed, the reaction can be stopped at a conversion of about 50% to about 60%. More preferably, the reaction is stopped at a conversion of about 50% to about 55%. The reaction can be stopped by addition of an organic solvent. Preferably, a water immiscible organic solvent, such as ethyl acetate, is added. The reaction can also be stopped by standard methods known to a person skilled in the art such as temperature increase, addition of acid or base and the like.

If esterase EstC from *Burkholderia gladioli* is employed, the reaction can be stopped at a conversion of about 40% to about 50%. More preferably, the reaction is stopped at a conversion of about 45% to about 50%. The reaction can be stopped by addition of an organic solvent. Preferably, a water immiscible organic solvent such as ethyl acetate is added.

If *Candida Antarctica* B is employed, the reaction is can be stopped at a conversion of about 40% to about 50%. More preferably, the reaction is stopped at a conversion of about 45% to about 50%. The reaction can be stopped by addition of an organic solvent. Preferentially a water immiscible organic solvent such as ethyl acetate is added. Preferably, the pH is above 7.4.

The amount of conversion can be determined by any suitable method, such as by measuring the amount of consumed base or by HPLC measurements.

After or during the stereoselective enzymatic hydrolysis, the unreacted enantiomer of 5-methyl-3-nitromethyl-hexanoic acid ester (VIII) (for example, (S)-5-methyl-3-nitromethyl-hexanoic acid ester S-(VIII)) and the resultant enantiomer of 5-methyl-3-nitromethyl-hexanoic acid salt (IX) (for example, (R)-5-methyl-3-nitromethyl-hexanoic acid salt R-(IX)) can be separated. For instance, the unreacted enantiomer of 5-methyl-3-nitromethyl-hexanoic acid ester (VIII) can be removed from the reaction mixture by one or more extractions with an organic solvent, which is not miscible with water, such as ethyl acetate or heptane, so that the resultant enantiomer of 5-methyl-3-nitromethyl-hexanoic acid salt (IX) remains in the aqueous layer.

Optionally, the undesired enantiomer (e.g. in the case of pregabalin the R-enantiomer) can be submitted to a racemization process and recycled into the stereoselective enzymatic hydrolysis process.

Although the stereoselective enzymatic hydrolysis can be employed in a variety of processes it is particularly well suited for the preparation of enantioenriched or enantiopure 3-(aminomethyl)-5-methylhexanoic acid (I), in particular pregabalin.

Reaction (h)

Reaction (h) is disclosed with respect to the reaction of the (S)-enantiomer. However, it should be understood that all of the explanations equally apply to the (R)-enantiomer.

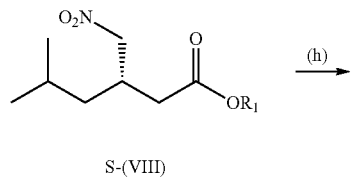

S-(VIII)

(h) →

-continued

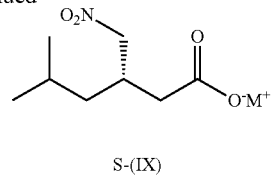

S-(IX)

In this reaction $R_1$ and $R_2$ are as defined above. The cation $M^+$ of the salt can be any suitable cation, such as an alkali or alkaline earth cation. It will be typically determined by the conditions under which the reaction is conducted and will, in particular, correspond to the cation of the base which is usually employed.

(S)-5-methyl-3-nitromethyl-hexanoic acid ester S-(VIII) can be reacted to the corresponding (S)-5-methyl-3-nitromethyl-hexanoic acid salt S-(IX) by alkaline hydrolysis. This reaction can carried out using, e.g. an aqueous solution of a base. Bases which are suitable for this purpose include, e.g. alkali or alkaline earth hydroxides, alkali or alkaline earth carbonates, and alkali or alkaline earth oxides. The base is typically employed in an amount in excess of (S)-5-methyl-3-nitromethyl-hexanoic acid ester S-(VIII), preferably the amount of the base is from about 2 eq. to about 4 eq., more preferably 2 eq. to about 2.2 eq., relative to 1 eq. of (S)-5-methyl-3-nitromethyl-hexanoic acid ester (VIII).

The reaction can take place at any suitable temperature. For example, it can be in the range of about 0° C. to about 50° C., more preferably in the range of about 20° C. to about 30° C. If the temperature is lower than about 20° C. the rate of reaction is reduced.

The yield of reaction (h) is usually about 90% or more.

The resultant (S)-5-methyl-3-nitromethyl-hexanoic acid salt S-(IX) can be isolated, e.g., by removal of the solvent and crystallization, or be further processed without isolation. Preferably, (S)-5-methyl-3-nitromethyl-hexanoic acid salt S-(IX) is directly reacted to (S)-3-(aminomethyl)-5-methyl-hexanoic acid (I) without previous isolation. Alternatively, the aqueous solution of (S)-5-methyl-3-nitromethyl-hexanoic acid salt (IX) can be washed with a water-immiscible solvent to remove non-polar impurities prior to reaction (i).

5-methyl-3-nitromethyl-hexanoic acid in the free acid form is prone to an irreversible rearrangement giving a compound of formula (XIII). This rearrangement does not take place if the corresponding salts, 5-methyl-3-nitromethyl-hexanoic acid salt (IX), are used.

(XIII)

The formation of this side product reduces the yield of the reaction. In order to suppress the formation of compound (XIII) the pH should generally be kept in the range of about 8 to about 14, preferably in the range of about 9 to about 10, during reaction (h).

By controlling the pH in the above mentioned range (S)-5-methyl-3-nitromethyl-hexanoic acid salt (IX) substantially free of compound (XIII) can be obtained, which can be further transformed to (S)-3-(aminomethyl)-5-methylhexanoic acid (I), which is substantially free of compound (XIII).

Reaction (i)

Reaction (i) is disclosed with respect to the reaction of the (S)-enantiomer. However, it should be understood that all of the explanations equally apply to the (R)-enantiomer.

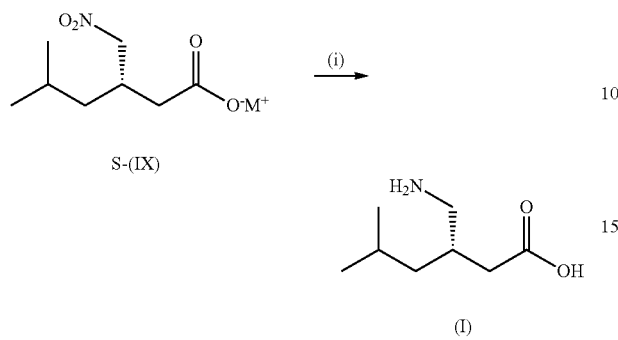

In this reaction M is as defined above.

(S)-5-Methyl-3-nitromethyl-hexanoic acid salt S-(IX) can be reduced to (S)-3-(aminomethyl)-5-methylhexanoic acid (I) (pregabalin) by any suitable method. Examples of possible methods include but are not limited to catalytic hydrogenation using gaseous hydrogen in the presence of a suitable transition metal catalyst such as Pt, $PtO_2$, Pd, Rh, Ru, Ni, or Raney Ni, optionally on a solid support such as carbon, silica, or calcium carbonate; Zn, Sn, or Fe in the presence of an acid; complex hydrides such as $LiAlH_4$, $AlH_3/AlCl_3$, $NaBH_4$ or $NaBH_4$ in combination with a salt; or a catalytic transfer hydrogenation using a hydrogen donor such as formic acid or salts thereof, hydrazine, 1,4-cyclohexadiene, cyclohexene, cis-decalin or silanes in the presence of a transition metal catalyst as defined above; or sulfides such as NaHS, $Ne_2S$, $(NH_4)_2S$, or polysulfides. Preferably, the reduction is carried out with gaseous hydrogen and Raney Nickel as a catalyst.

In order to avoid the formation of the undesired side product (XIII) the pH should be kept in the range of about 8 to about 14, preferably in the range of about 9 to about 14, during reaction (i), too.

The product mixture of a chemical reaction is rarely a single compound with sufficient purity to comply with pharmaceutical standards. Side products and by-products of the reaction and adjunct reagents used in the reaction will, in most cases, also be present in the product mixture. At certain stages during processing of an API, such as (S)-pregabalin, reaction products must be analyzed for purity, typically, by HPLC or TLC analysis, to assess suitability for continued processing and, ultimately, for use in a pharmaceutical product. The API need not be absolutely pure, as absolute purity is a theoretical ideal that is typically unattainable. Rather, purity standards are set with the intention of ensuring that an API is as free of impurities as possible, and, thus, is as safe as possible for clinical use. As discussed above, national guidelines recommend that the amounts of some impurities be limited to less than 0.1%.

Using the processes described as above, by products such as compound X are present in the API with more than 0.1%.

Reaction (j)

Reaction (j) is disclosed with respect to the reaction of the (S)-enantiomer. However, it should be understood that all of the explanations equally apply to the (R)-enantiomer.

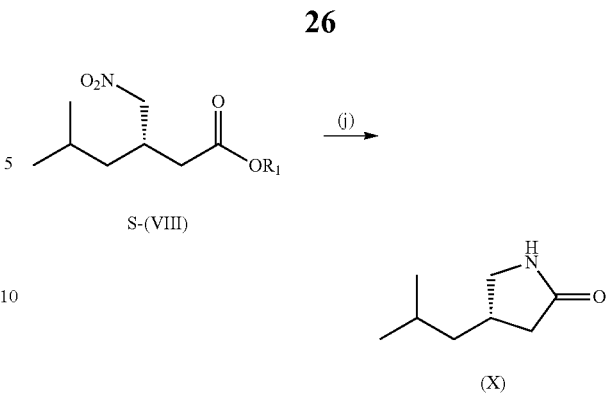

In reaction (j) the definition of $R_1$ given above applies.

(S)-5-Methyl-3-nitromethyl-hexanoic acid ester S-(VIII) can be reacted to the corresponding enantiomer of lactam (X) using various methods. The reduction of racemic 5-methyl-3-nitromethyl-hexanoic acid ester rac-(VIII) to racemic 3-(aminomethyl)-5-methylhexanoic acid rac-(I) is described in Andruszkiewicz, R.; Silverman, R. B. *Synthesis* 1989, 953-955. In this publication the reduction is carried out using hydrogen with Pd/C as catalyst.

The reduction of (S)-5-methyl-3-nitromethyl-hexanoic acid ester S-(VIII) can be carried out using this process. However, other methods for reducing the nitro group under different conditions are also applicable. Examples include, but are not limited to, catalytic hydrogenation using gaseous hydrogen in the presence of a suitable transition metal catalyst such as Pt, $PtO_2$, Pd, Rh, Ru, Ni, or Raney Ni, optionally on a solid support such as carbon, silica, or calcium carbonate; Zn, Sn, or Fe in the presence of an acid; complex hydrides such as $LiAlH_4$, $AlH_3/AlCl_3$, $NaBH_4$ or $NaBH_4$ in combination with a salt; or a catalytic transfer hydrogenation using a hydrogen donor such as formic acid or salts thereof, hydrazine, 1,4-cyclohexadiene, cyclohexene, cis-decalin or silanes in the presence of a transition metal catalyst as defined above; or sulfides such as NaHS, $Na_2S$, $(NH_4)_2S$, or polysulfides.

Reaction (k)

Reaction (k) is described with respect to the reaction of the (S)-enantiomer. However, it should be understood that all of the explanations equally apply to the (R)-enantiomer.

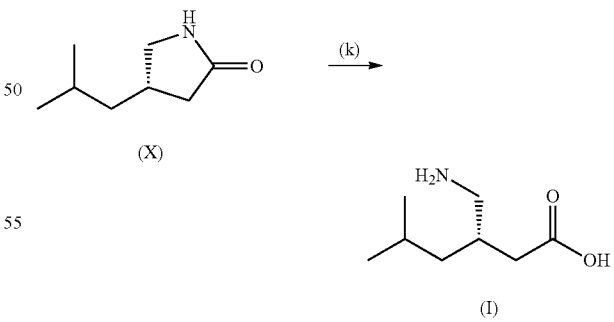

The enantiomer of lactam (X) can be hydrolyzed to (S)-3-(aminomethyl)-5-methylhexanoic acid S-(I) using appropriate reaction conditions. In the reference by Andruszkiewicz, R. and Silverman, R. B. (*Synthesis* 1989, 953-955) refluxing in 6N aqueous HCl for 3 hours can be used for this reaction. However, it is also possible to hydrolyze lactam X in the presence of base such as aqueous NaOH.

Reaction (m)

Reaction (m) is described with respect to the reaction of the (S)-enantiomer. However, it should be understood that all of the explanations equally apply to the (R)-enantiomer.

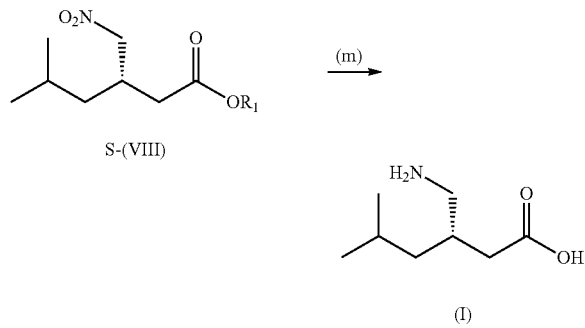

The definition of $R_1$ given above applies analogously in reaction (m).

Another method, which is disclosed in WO 2008/007145, describes the reduction of racemic 5-methyl-3-nitromethyl-hexanoic acid ester (VIII) to racemic 3-(aminomethyl)-5-methylhexanoic acid (I). The reduction transforms the nitro group to the amine and at the same time reductively cleaves the benzylic ester. A corresponding reaction can be applied to the enantiomeric form of 5-methyl-3-nitromethyl-hexanoic acid ester (VIII).

Isolation of 3-(aminomethyl)-5-methylhexanoic acid (I)

Regardless of how the desired enantiomer of 3-(aminomethyl)-5-methylhexanoic acid (I) is formed it is preferably isolated from the reaction mixture. Any suitable method can be employed such as those described, e.g., in the prior art (see for instance WO 2005/100580, WO 2006/00904, EP-A-828704, or EP-A-830338). Preferably, 3-(aminomethyl)-5-methylhexanoic acid (I) is isolated by crystallization from water or water in combination with an organic solvent such as 2-propanol.

The following examples are given to illustrate the present invention. They should not be construed as limiting the scope of the invention which is solely defined by the appended claims.

EXAMPLES

Example 1

Synthesis of 2-(3-methyl-butylidene)-malonic acid diethyl ester (XI, $R_1=R_2$=ethyl)

3-Methylbutyraldehyde (145.2 g; 1.69 mol, compound VI) was dissolved in 400 mL of hexane.

9.6 g of acetic acid (0.16 mol) and 8.1 g of di-n-propylamine (0.08 mol) were added. To this solution 256.3 g (1.60 mol) of diethylmalonate were added. The reaction mixture was heated to reflux. Water was continuously removed using a Dean Stark trap until complete conversion of the starting material was observed. The reaction mixture was cooled to room temperature and was washed twice with 200 mL of water, once with 160 mL of 1M aqueous NaOH, and once with 5% aqueous $NH_4Cl$. The organic layer was dried by azeotropic distillation and the solvent was removed under reduced pressure to give 374 g of crude 2-(3-methyl-butylidene)-malonic acid diethyl ester (97% yield; compound XI, $R_1=R_2$=Et). A small part of the crude product was purified by vacuum distillation (bp 95° C., 1 mbar).

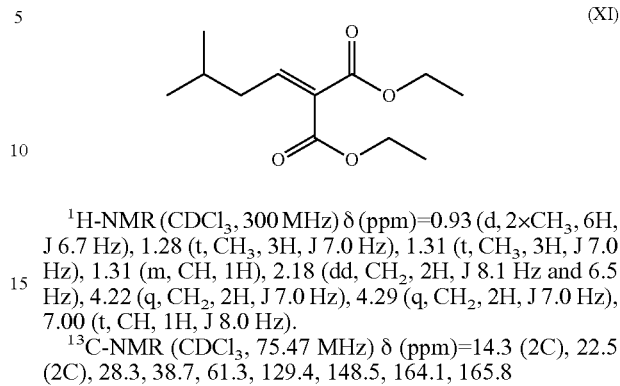

$^1$H-NMR ($CDCl_3$, 300 MHz) δ (ppm)=0.93 (d, 2×$CH_3$, 6H, J 6.7 Hz), 1.28 (t, $CH_3$, 3H, J 7.0 Hz), 1.31 (t, $CH_3$, 3H, J 7.0 Hz), 1.31 (m, CH, 1H), 2.18 (dd, $CH_2$, 2H, J 8.1 Hz and 6.5 Hz), 4.22 (q, $CH_2$, 2H, J 7.0 Hz), 4.29 (q, $CH_2$, 2H, J 7.0 Hz), 7.00 (t, CH, 1H, J 8.0 Hz).

$^{13}$C-NMR ($CDCl_3$, 75.47 MHz) δ (ppm)=14.3 (2C), 22.5 (2C), 28.3, 38.7, 61.3, 129.4, 148.5, 164.1, 165.8

Example 2

Synthesis of 2-(3-methyl-1-nitromethyl-butyl)-malonic acid diethyl ester (XII, $R_1$=ethyl)

2-(3-Methyl-butylidene)-malonic acid diethyl ester (30.0 g, 0.131 mol, compound XII, $R_1$=ethyl) was dissolved in 35 mL of nitromethane. The solution was cooled to 0° C. and 3.3 mL of 1,1,3,3-tetramethylguanidine (0.026 mol) were added within 30 minutes. The reaction mixture was stirred at 0° C. for one hour and then for four hours at 25° C. GC analysis indicated complete conversion. 40 mL of 2M aqueous HCl were added and after stirring for 5 minutes the layers were separated (20 mL of saturated aqueous NaCl were added to facilitate the layer separation). The aqueous layer was washed twice with 100 mL of methyl tert-butyl ether. The combined organic layers were washed once with 50 mL of saturated aqueous $NaHCO_3$ and 25 mL of water. The organic phase was dried and thereafter concentrated under reduced pressure to give 2-(3-methyl-1-nitromethyl-butyl)-malonic acid diethyl ester (XII, $R_1=R_2$=ethyl) as a slightly yellow oil (37.8 g, 99% yield).

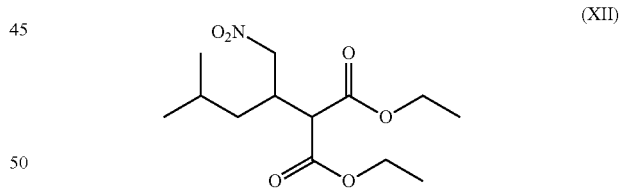

$^1$H-NMR ($CDCl_3$, 300 MHz) δ (ppm)=0.90 (d, $CH_3$, 3H, J 7.0 Hz), 0.91 (d, $CH_3$, 3H, J 7.0 Hz), 1.26 (t, 2×$CH_3$, 6H, J 7.0 Hz), 1.63 (m, CH, 1H), 2.94 (m, CH, 1H), 3.60 (d, CH, 1H, J 5.7 Hz), 4.20 (q, 2×$CH_2$, 4H, J 7.0 Hz), 4.50 (dd, $CH_2$, 1H, J 7.0 Hz and 14 Hz), 4.69 (dd, $CH_2$, 1H, J 5.0 Hz and 14 Hz).

$^{13}$C-NMR ($CDCl_3$, 75.47 MHz) δ (ppm)=14.1 (2C), 22.3, 22.4, 25.1, 34.9, 39.0, 52.8, 61.9, 62.0, 76.9, 167.9, 168.1.

Example 3

Synthesis of 5-methyl-3-nitromethyl-hexanoic acid ethyl ester (VIII, $R_1=R_2$=ethyl)

10.0 g (34 mmol) of 2-(3-methyl-1-nitromethyl-butyl)-malonic acid diethyl ester (XII, $R_1$=ethyl) were dissolved in 140 mL of DMSO. Water (10.4 mL) and solid NaCl (14.6 g) were added and the mixture was heated for 6 hours at 150° C. After complete conversion, the reaction mixture was cooled to 25° C. and 150 mL of methyl tert-butyl ether were added. 100 mL of water were added slowly. The heterogeneous mixture was stirred for 5 minutes prior to layer separation. The aqueous layer was washed once with 75 mL of methyl tert-butyl ether. The organic layers were combined and washed once with 50 mL of water. The combined organic layers were dried and the volatiles were removed under reduced pressure to give 7.0 g of 5-methyl-3-nitromethyl-hexanoic acid ethyl ester (VIII, $R_1$=ethyl; 93% yield).

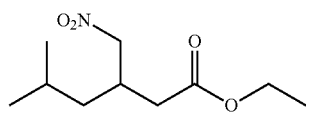

(VIII)

$^1$H-NMR (CDCl$_3$, 300 MHz) δ (ppm)=0.78 (t, 2×CH$_3$, 6H, J 7.0 Hz), 1.12 (t, CH$_2$, 2H, J 7.0 Hz), 1.13 (t, CH$_3$, 3H, J 7.0 Hz), 1.52 (m, CH, 1H), 2.29 (d, CH$_2$, 2H, J 6.6 Hz), 2.54 (m, CH, 1H), 4.01 (q, CH$_2$, 2H, J 7.2 Hz), 4.29 (dd, CH$_2$, 1H, J 5.7 Hz and 12.4 Hz), 4.36 (dd, CH$_2$, 1H, J 6.8 Hz and 12.4 Hz).

$^{13}$C-NMR (CDCl$_3$, 75.47 MHz) δ (ppm)=14.2, 22.3, 22.6, 25.1, 36.1, 40.6, 60.8, 78.9, 171.6.

Example 4

Synthesis of 5-methyl-3-nitromethyl-hexanoic acid ethyl ester (VIII, $R_1$=ethyl)

5.0 g (21.9 mmol) of 2-(3-methylbutylidene)-malonic acid diethyl ester (compound XI, $R_1$=$R_2$=Et) were dissolved in 35 mL of DMSO. 2.6 mL of water and 3.65 g of NaCl were added. The heterogeneous mixture was stirred for 7 hours at 150° C. to give, after filtration, 55 g of a solution of 5-methyl-hex-2-enoic acid ethyl ester (VII, $R_1$=ethyl) in DMSO.

7.0 g of nitromethane and 3.3 mL of DBU (1,8-diazabicyclo[5.4.0]undec-7-en) were added to the DMSO solution of α,β-unsaturated ester VII. The reaction mixture was stirred until complete conversion was detected by GC. 20 mL of CH$_2$Cl$_2$ were added and the resulting mixture was washed with 2×20 mL of 1M aqueous H$_2$SO$_4$ and 1×20 mL of 0.5M aqueous NaHCO$_3$. The organic layer was dried and the solvent was removed under reduced pressure. 3.6 g of γ-nitroester VIII were obtained (yield over two steps: 75%).

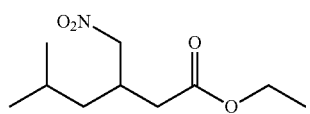

(VIII)

$^1$H-NMR (CDCl$_3$, 300 MHz) δ (ppm)=0.76 (d, CH$_3$, 3H, J 7.0 Hz), 0.80 (d, CH$_3$, 3H, J 7.0 Hz), 1.12 (t, CH$_2$, 2H, J 7.0 Hz), 1.13 (t, CH$_3$, 3H, J 7.0 Hz), 1.52 (m, CH, 1H), 2.29 (d, CH$_2$, 2H, J 6.6 Hz), 2.54 (m, CH, 1H), 4.01 (q, CH$_2$, 2H, J 7.2 Hz), 4.29 (dd, CH$_2$, 1H, J 5.7 Hz and 12.4 Hz), 4.36 (dd, CH$_2$, 1H, J 6.8 Hz and 12.4 Hz).

$^{13}$C-NMR (CDCl$_3$, 75.47 MHz) δ (ppm)=14.2, 22.3, 22.6, 25.1, 36.1, 40.6, 60.8, 78.9, 171.6.

Example 5

Synthesis of 5-methyl-hex-2-enoic acid ethyl ester (VII, $R_1$=ethyl)

3-Methylbutyraldehyde (64 mL; 0.58 mol, compound VI) was added to 115 g (0.87 mol) of monoethylmalonate in 165 mL (2.0 mol) of pyridine. To this solution 0.15 mL (0.25 mol %) of piperidine were added. The reaction mixture was heated to 80° C. and stirred at this temperature for 90 minutes. GC analysis indicated complete consumption of the starting material.

Methyl tert-butyl ether (200 mL) was added and the organic layer was washed three times with 150 mL of 2M aqueous H$_2$SO$_4$, then twice with 100 mL of 0.5M aqueous NaHCO$_3$. The solvent was removed under reduced pressure to give 85.6 g of substantially pure α,β-unsaturated ester VII (GC purity >99%; E/Z 6/1; yield 94%).

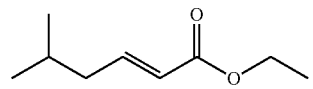

(VII)

$^1$H-NMR of major isomer (CDCl$_3$, 300 MHz) δ (ppm) =0.91 (d, 2×CH$_3$, 6H, J 7.0 Hz), 1.27 (t, CH$_3$, 3H, J 7.1 Hz), 1.73 (m, CH, 1H), 2.06 (bt, CH$_2$, 2H, J 7.0 Hz), 4.16 (q, CH$_2$, 2H. 7.1 Hz), 5.78 (bd, CH, 1H, J 15.6 Hz), 6.92 (bt, CH, 1H, J 15.6 Hz, 7.7 Hz, and 7.4 Hz).

$^{13}$C-NMR of major isomer (CDCl$_3$, 75.47 MHz) δ (ppm) =14.4, 22.4, 27.9, 41.6, 60.2, 122.4, 148.4, 166.8.

Example 6

Synthesis of 5-methyl-3-nitromethyl-hexanoic acid ethyl ester (VIII, $R_1$=ethyl)

5-Methyl-hex-2-enoic acid ethyl ester (VII, $R_1$=ethyl) (123.9 g; 0.79 mol) was dissolved in 112 mL (1.98 mol) of nitromethane. To this solution 36 mL of DBU (0.24 mol) were added. The reaction mixture was heated to 60° C. and stirred at this temperature for 150 minutes. GC analysis indicated complete consumption of the starting material.

Methyl tert-butyl ether (100 mL) was added and the organic layer was washed with 200 mL of 2M aqueous HCl. The aqueous layer was extracted twice with 50 mL of methyl tert-butyl ether. The organic layers were combined and washed with 50 mL of saturated aqueous NaHCO$_3$. The solvent was removed under reduced pressure to give 172.4 g of substantially pure γ-nitro ester VIII (GC purity >97%; yield 98%).

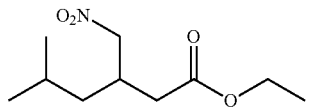

(VIII)

$^1$H-NMR (CDCl$_3$, 300 MHz) δ (ppm)=0.78 (t, 2×CH$_3$, 6H, J 7.0 Hz), 1.12 (t, CH$_2$, 2H, J 7.0 Hz), 1.13 (t, CH$_3$, 3H, J 7.0 Hz), 1.52 (m, CH, 1H), 2.29 (d, CH$_2$, 2H, J 6.6 Hz), 2.54 (m, CH, 1H), 4.01 (q, CH$_2$, 2H, J 7.2 Hz), 4.29 (dd, CH$_2$, 1H, J 5.7 Hz and 12.4 Hz), 4.36 (dd, CH$_2$, 1H, J 6.8 Hz and 12.4 Hz).

13C-NMR (CDCl$_3$, 75.47 MHz) δ (ppm)=14.2, 22.3, 22.6, 25.1, 36.1, 40.6, 60.8, 78.9, 171.6.

Example 7

Synthesis of (S)-5-methyl-3-nitromethyl-hexanoic acid ethyl ester (VIII, R$_1$=ethyl) and (R)-5-methyl-3-nitromethyl-hexanoic acid sodium salt (IX)

100 g of 5-methyl-3-nitromethyl-hexanoic acid ethyl ester (VIII, R$_1$=ethyl) were added to an aqueous solution of EstB (500 mL cell extract; ~5 g total protein concentration). At a temperature of 25° C. the pH was kept at 7.0 by continuous addition of 5M aqueous NaOH. After 55% conversion (corresponds to 50.6 mL of NaOH consumption) the reaction was stopped by addition of 100 mL of ethyl acetate. 100 mL of 5M aqueous NaOH were added and the layers were separated. The aqueous layer was washed once with 100 mL of ethyl acetate. The combined organic layers were concentrated under reduced pressure to give 43 g of (S)-5-methyl-3-nitromethyl-hexanoic acid ethyl ester (VIII, R$_1$=ethyl; ee=98%).

Example 8

Synthesis of (R)-5-methyl-3-nitromethyl-hexanoic acid ethyl ester (VIII, R$_1$=ethyl) and (S)-5-methyl-3-nitromethyl-hexanoic acid sodium salt (IX)

100 g of 5-methyl-3-nitromethyl-hexanoic acid ethyl ester (VIII, R$_1$=ethyl) were added to an aqueous solution of EstC (250 mL cell extract; ~10 g total proteine concentration). At a temperature of 5 to 10° C. the pH was kept at 9.0 by continuous addition of 5M aqueous NaOH. After 45% conversion (corresponding to 41.4 mL of NaOH consumption) the reaction was stopped by addition of 100 mL of ethyl acetate. 100 mL of 5M aqueous NaOH were added and the layers were separated. The aqueous layer was washed once with 100 mL of ethyl acetate. The combined aqueous layer were filtered and concentrated under reduced pressure to give about 200 mL of a solution of (S)-5-methyl-3-nitromethyl-hexanoic acid potassium salt in water (ee=92%).

Example 8a

Synthesis of (S)-5-methyl-3-nitromethyl-hexanoic acid sodium salt (IX)

In a beaker 100 mg of EstC (lyophilized) were dissolved/suspended in 10 mL of potassium phosphate buffer (1 mM, pH 7.2). The pH drops to pH ~6.8 and was adjusted to pH=7.4 with aqueous NaOH (0.1 M). Then 200 mg of 5-methyl-3-nitromethyl-hexanoic acid ethyl ester (VIII, R1=ethyl) were added and the pH was kept at 7.4 by continuous addition of aqueous NaOH (0.1M). After 45% conversion (corresponding to 4.0 mL of 0.1M NaOH consumption) the reaction was stopped by addition of 10 mL of ethyl acetate. The layers were separated and the aqueous layer was extracted once more with 10 mL of ethyl acetate. Then the aqueous layer was concentrated to give the title compound with an ee of 88%.

Example 8b

Synthesis of (S)-5-methyl-3-nitromethyl-hexanoic acid sodium salt (IX)

In a beaker 100 mg of EstC (lyophilized) were dissolved/suspended in 10 mL of potassium phosphate buffer (1 mM, pH 7.2). The pH drops to pH ~6.8 and was adjusted to pH=7.4 with aqueous NaOH (0.1 M). Then 250 μL of methanol and 200 mg of 5-methyl-3-nitromethyl-hexanoic acid ethyl ester (VIII, R1=ethyl) were added and the pH was kept at 7.4 by continuous addition of aqueous NaOH (0.1M). After 45% conversion (corresponding to 4.0 mL of 0.1M NaOH consumption) the reaction was stopped by addition of 10 mL of ethyl acetate. The layers were separated and the aqueous layer was extracted once more with 10 mL of ethyl acetate. Then the aqueous layer was concentrated to give the title compound with an ee of 98%.

Example 9

Synthesis of (S)-3-aminomethyl-5-methyl-hexanoic acid (I, pregabalin)

150 g of (S)-5-methyl-3-nitromethyl-hexanoic acid ethyl ester (VIII, R$_1$=ethyl; assay: 97.2%) were suspended in 300 mL of H$_2$O. KOH (90.1.g, assay 86.1%, 2.05 eq.) was added. The initially turbid reaction mixture became clear which indicated that the reaction was nearly completed. After complete conversion (as determined by HPLC) the reaction mixture was transferred to a hydrogenation reactor. 90.0 g of an aqueous slurry of Raney Nickel were added. At a hydrogen pressure of 12 bar and a temperature of 45° C. the mixture was stirred until complete conversion was detected by HPLC giving 88.0 g of pregabalin in an aqueous solution.

The solution was filtered and then concentrated to about 270 g under reduced pressure and 400 mL of 2-propanol were added. At a temperature of 45° C. acetic acid was added until a pH of 7.0 was reached. Pregabalin started to crystallize. Within about 60 minutes the reaction mixture was cooled down to 10° C. Stirring was continued for 1 hour, then the product was isolated by filtration. The filter cake was washed with 90 mL of a 1:1 mixture of cold H$_2$O/2-propanol. After drying 75 g of substantially pure pregabalin (purity 99.6%) were obtained (yield: 70%).

A part of pregabalin was recrystallized as described in WO 2006/000904 to increase the purity from 99.6% to 99.9%. The analytical data were in accordance with those reported in literature.

Example 10

Synthesis of (S)-3-aminomethyl-5-methyl-hexanoic acid (I, pregabalin)

150 g of (S)-5-methyl-3-nitromethyl-hexanoic acid ethyl ester (VIII, R$_1$=ethyl; assay: 97.2%) were suspended in 300 mL of H$_2$O. KOH (90.1.g, assay 86.1%, 2.05 eq.) was added. The initially turbid reaction mixture became clear which indicated that the reaction was nearly completed. After complete conversion (determined by HPLC) NH$_4$-formate and Pd/C were added. The reaction mixture was stirred until complete conversion was observed. The solution was filtered and then concentrated to about 250 g under reduced pressure and 400 mL of 2-propanol were added. At a temperature of 45° C. acetic acid was added until a pH of 7.0 was reached. Pregabalin started to crystallize. Within about 60 minutes the reaction mixture was cooled down to 10° C. Stirring was continued for 1 hour, then the product was isolated by filtration. The filter cake was washed with 90 mL of a 1:1 mixture of cold H$_2$O/2-propanol. After drying, 65 g of substantially pure pregabalin (purity 97.9%) were obtained (yield: 61%).

Example 11

(S)-5-Methyl-3-nitromethyl-hexanoic acid dipotassium salt (IX—dipotassium-salt)

830 mg of (S)-5-methyl-3-nitromethyl-hexanoic acid ethyl ester (VIII, $R_1$=ethyl) were suspended in 0.8 mL of $H_2O$. 900 mg of 50% aqueous KOH were added. After 5 h at 25° C. conversion was complete (determination by HPLC). The solvent was removed under reduced pressure to give a solid consisting of the title compound and minor amounts of KOH.

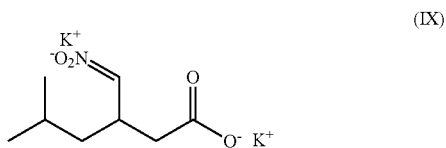

(IX)

$^{13}$C-NMR ($D_2O$, δ5.47 MHz) δ (ppm)=21.9, 22.8, 26.0, 33.9, 40.9, 41.6, 123.5, 181.7.

Example 12

(S)-5-Methyl-3-nitromethyl-hexanoic acid monopotassium salt (IX—monopotassium salt)

830 mg of (S)-5-methyl-3-nitromethyl-hexanoic acid ethyl ester (VIII, $R_1$=ethyl) were suspended in 0.8 mL of $H_2O$. 900 mg of 50% aqueous KOH were added. After 5 h at 25° C. conversion was complete (determination by HPLC). 4.2 mL of 1M aqueous HCl were added and the solvent was removed under reduced pressure to give a solid consisting of the title compound and KCl.

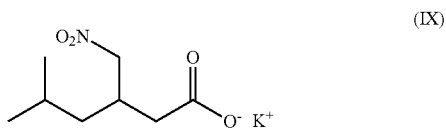

(IX)

$^{13}$C-NMR ($D_2O$, δ5.47 MHz) δ (ppm)=23.0, 23.3, 25.2, 32.5, 36.7, 41.0, 79.9, 173.8.

Example 13

Synthesis of (S)-3-aminomethyl-5-methyl-hexanoic acid (I, pregabalin)

For the reduction with Raney-Nickel 5.0 g of (S)-5-methyl-3-nitromethyl-hexanoic acid ethyl ester (VIII, $R_1$=ethyl) were dissolved in 10 mL of ethanol and 0.4 mL of water and 3.0 g of an aqueous slurry of Raney-Ni were added. The reaction mixture was stirred at 40° C. under 4 bar hydrogen pressure. The reaction was filtered after complete conversion of the starting material and the solvent was removed under reduced pressure to give 3.02 g of crude lacton X as an oily residue, which crystallized upon standing.

30 mL of 6N aqueous HCl were added to the crude lacton and the reaction mixture was heated to reflux. After 4 h the reaction mixture was concentrated under reduced pressure to give 4 g of an oily residue. Water (5 mL) was added and the pH was adjusted to 6 by addition of 50% aqueous KOH. The mixture was heated to 50° C. and slowly cooled down to 10° C. The formed crystals were isolated by filtration. Concentration of the mother liquor gave a second crystal crop yielding 2.5 g of pregabalin (72%).

Example 14

Synthesis of (S)-3-aminomethyl-5-methyl-hexanoic acid (I, pregabalin)

(S)-5-Methyl-3-nitromethyl-hexanoic acid ethyl ester (VIII, $R_1$=ethyl) (10.4 g) were dissolved in 160 mL of MeOH. 4 g of 10% Pd/C and 20 g of ammonium formate were added. After a few minutes an exothermic reaction was observed. After 30 minutes HPLC analysis indicated complete conversion. The catalyst was removed by filtration. The filtrate was concentrated under reduced pressure to a volume of about 20 mL. Water (20 mL) was added, then the solution was again concentrated unter reduced pressure to about 20 mL. Then 50 mL of 6N aqueous HCl were added and the mixture was refluxed for 6 hours. After complete conversion, the reaction mixture was concentrated under reduced pressure to about 20 mL. Water (20 mL) and 2-propanol (40 mL) were added and the reaction mixture was heated to 45° C. KOH was added until a pH of 7 was reached. The product started to crystallize. Within about 60 minutes the reaction mixture was cooled down to 10° C. Stirring was continued for 1 hour, then the product was isolated by filtration. The filter cake was washed with 90 mL of a 1:1 mixture of cold $H_2O$/2-propanol. After drying, 5.9 g of substantially pure pregabalin (purity 98.0%) were obtained (yield: 81%).

A part of pregabalin was recrystallized as described in WO 2006/000904 to increase the purity from 98.0% to 99.9%.

Example 15

Synthesis of (S)-3-aminomethyl-5-methyl-hexanoic acid (I, pregabalin)

3-Methylbutyraldehyde (100 mL; 0.91 mol, compound VI) was added to 180 g (1.36 mol) of monoethylmalonate in 260 mL (3.1 mol) of pyridine. To this solution 0.23 mL (0.25 mol %) of piperidine were added. The reaction mixture was heated to 80° C. and stirred at this temperature for 90 minutes. GC analysis indicated complete consumption of the starting material.

Methyl tert-butyl ether (300 mL) was added and the organic layer was washed three times with 200 mL of 2M aqueous $H_2SO_4$, then twice with 150 mL of 0.5M aqueous $NaHCO_3$. A major part of the solvent was removed under reduced pressure and nitromethane (120 mL) was added. To this solution 40 mL of DBU were added. The reaction mixture was heated to 60° C. and stirred at this temperature for 150 minutes. GC analysis indicated complete consumption of the starting material.

Methyl tert-butyl ether (100 mL) was added and the organic layer was washed with 200 mL of 2M aqueous HCl. The aqueous layer was extracted twice with 50 mL of methyl tert-butyl ether. The organic layers were combined and washed with 50 mL of saturated aqueous $NaHCO_3$. DBU was recovered from the aqueous layer by addition of 50% aqueous NaOH and extraction with methyl tert-butyl ether (recovery yield after two extractions each with 100 mL of methyl tert-butyl ether was 75%; pH of aqueous layer >12).

The solvent of the organic layer was removed under reduced pressure to give 188.2 g of substantially pure γ-nitro ester VIII (GC purity >95%; methyl tert-butyl ether <5%).

The ester can be transformed into pregabalin as described in examples 7, 8, and 9.

Example 16

Rapid Screening for Suitable Enzymes Using Commercially Available Enzymes

The enzyme screening was carried as described in M. Ivancic et al., J. of Biotechnology 2007, 129, 109-122, the complete disclosure of which is herein incorporated by reference for all purposes. All enzymes were obtained from Sigma-Aldrich (St. Louis, Mo.), Fluka (Buchs, Switzerland), Amano (Nagoya, Japan), Novo Nordisk (Bagsvaerd, Denmark), Bio-Catalytics/Codexis or from the Technical University of Graz.

For analysis of the commercially available esterases or lipases a rapid screening assay based on pH shift was used. This assay was performed in two steps: (i) active enzymes were identified; (ii) active enzymes were further analyzed with respect to their activities towards the R- and S-enantiomers of 5-methyl-3-nitromethyl-hexanoic acid ethyl ester.

Solutions of the individual enzymes were placed onto filter papers and dried at 30° C. for 30 min. Dried filter papers were soaked with screening solution containing Triton X 100 (0.6%), phenol red (2 gL$^{-1}$), Tris-HCl buffer pH=7.5 and 50 mM of racemic 5-methyl-3-nitromethyl-hexanoic acid ethyl ester. Hydrolysis of the ester was monitored visually by the change of color from red to yellow due to pH drop caused by released acid. Positive hits showing esterase activity were selected and analyzed further, by placing them on filter paper, which was dried and than soaked with R and S screening solutions which contained instead of racemic, the pure enantiomers as substrates. Activity of enzymes was monitored on the basis of the time needed for the colour change of the pH indicator.

Selected enzymes were analyzed further by running the enzymatic hydrolysis at a preparative scale using 200 mg of racemic substrate in 5 mL of Tris-HCl buffer at pH=7.5. The enzyme preparation was added in a sufficient amount to have reaction times of less than 24 hours. The conversion was determined by measuring the amount of consumed 1M aqueous NaOH. At a consumption corresponding to 50% conversion the reaction was stopped by addition of 5 mL of ethyl acetate. The layers were separated and the organic layer was analyzed by chiral GC.

Example 17

Recombinant Expression of EstC from *Burkholderia gladioli* in *E. coli*

377 g *E. coli* cells over-expressing EstC from *Burkholderia gladioli* were suspended in 830 mL of 200 mM sodium phosphate/citrate (pH 7.0) and subjected twice towards homogenization. The cell suspension was diluted 1:2 with Sepipur® CL930 resulting in 4000 ppm flocculant. The esterase activity of the wet cells was determined using p-nitrophenyl acetate as substrate. Esterases are catalyzing the hydrolysis of p-nitrophenyl acetate into p-nitrophenol and acetic acid. The enzyme activity is determined by measuring the increase of absorption of p-nitrophenol (yellow, 404 nm) depending on the time. For the wet cells an activity of 826 U/g was measured. After centrifugation a clear crude lysate was obtained having a specific activity of 158 U/mL. The diluted crude lysate was concentrated using a ultrafiltration system from Pall corporation (Centramate™) with a cut-off membrane of 50 kDa. The concentration factor was 8, resulting in a retentate having a specific activity of 855 U/mL and a permeat having a specific activity of 6.3 U/mL. The lyophilization residue was 23.3 g and had a specific activity of 9125 U/g. The overall yield was 68.3%.

The invention claimed is:

1. A process for the stereoselective enzymatic hydrolysis of 5-methyl-3-nitromethyl-hexanoic acid ester (VIII) in which racemic 5-methyl-3-nitromethyl-hexanoic acid ester (VIII)

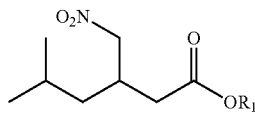

(VIII)

is contacted with an enzyme to result in the (R)-enantiomer of 5-methyl-3-nitromethyl-hexanoic acid ester (VIII) and form the (S)-enantiomer of a 5-methyl-3-nitromethyl-hexanoic acid salt, wherein $R_1$ is an alkyl, aryl or arylalkyl group, and wherein the enzyme is selected from the group consisting of esterase from hog liver, lipase A from *Candida Antarctica*, esterase from pig liver and esterase EstC from *Burkholderia gladioli*.

2. The process according to claim 1, wherein the enzyme is esterase EstC from *Burkholderia gladioli*.

3. The process according to claim 1, wherein conversion is from about 40% to about 50%.

4. The process according to claim 1, wherein the enantiomeric excess (ee) of the remaining 5-methyl-3-nitromethyl-hexanoic acid ester (VIII) or the formed 5-methyl-3-nitromethyl-hexanoic acid salt (IX) at a conversion of 50% is greater than 80%.

5. The process according to claim 4, wherein the enantiomeric excess (ee) of the remaining 5-methyl-3-nitromethyl-hexanoic acid ester (VIII) or the formed 5-methyl-3-nitromethyl-hexanoic acid salt (IX) at a conversion of 50% is greater than 95%.

6. The process according to claim 1, wherein the stereoselective enzymatic hydrolysis is conducted in an aqueous system comprising methanol.

7. The process according to claim 1, wherein the stereoselective enzymatic hydrolysis is conducted in an aqueous solution at a pH in the range of about 5 to about 11.

8. The process according to claim 1, further comprising separating the enantiomer of (R)-5-methyl-3-nitromethyl-hexanoic acid ester (VIII) from the (S)-5-methyl-3-nitromethyl-hexanoic acid salt, and further reacting the separated (S)-enantiomer of 5-methyl-3-nitromethyl-hexanoic acid salt to form 3-(aminomethyl)-5-methylhexanoic acid.

9. The process according to claim 8, wherein the separated (S)-enantiomer of 5-methyl-3-nitromethyl-hexanoic acid salt is reduced at a pH in the range of about 8 to about 14 to form the 3-(aminomethyl)-5-methylhexanoic acid.

10. The process according to claim 1, wherein the stereoselective enzymatic hydrolysis is conducted in an aqueous solution at a pH in the range of about 8 to about 14.

11. A process for the stereoselective enzymatic hydrolysis of 5-methyl-3-nitromethyl-hexanoic acid ester (VIII) in which racemic 5-methyl-3-nitromethyl-hexanoic acid ester (VIII)

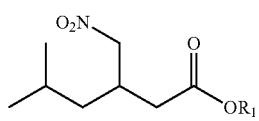

(VIII)

is contacted with an enzyme to result in the (S)-enantiomer of 5-methyl-3-nitromethyl-hexanoic acid ester (VIII) and form the (R)-enantiomer of a 5-methyl-3-nitromethyl-hexanoic acid salt, wherein $R_1$ is an alkyl, aryl or arylalkyl group, and wherein the enzyme comprises esterase EstB from *Burkholderia gladioli*.

* * * * *